United States Patent
Tabori et al.

(10) Patent No.: US 9,896,732 B2
(45) Date of Patent: Feb. 20, 2018

(54) METHOD OF DIAGNOSING CANCER COMPRISING DETECTION OF THE METHYLATION SIGNATURE IN THE HTERT PROMOTER

(71) Applicant: The Hospital for Sick Children, Toronto (CA)

(72) Inventors: Uri Tabori, Toronto (CA); Pedro Castelo-Branco, Toronto (CA)

(73) Assignee: The Hospital for Sick Children (CA)

( * ) Notice: Subject to any disclaimer, the term of this patent is extended or adjusted under 35 U.S.C. 154(b) by 148 days.

(21) Appl. No.: 14/403,802

(22) PCT Filed: May 24, 2013

(86) PCT No.: PCT/CA2013/000508
§ 371 (c)(1),
(2) Date: Nov. 25, 2014

(87) PCT Pub. No.: WO2013/173912
PCT Pub. Date: Nov. 28, 2013

(65) Prior Publication Data
US 2015/0232941 A1     Aug. 20, 2015

Related U.S. Application Data

(60) Provisional application No. 61/651,750, filed on May 25, 2012, provisional application No. 61/668,556, filed on Jul. 6, 2012.

(51) Int. Cl.
*C12Q 1/68*        (2006.01)

(52) U.S. Cl.
CPC ...... *C12Q 1/6886* (2013.01); *C12Q 2600/112* (2013.01); *C12Q 2600/118* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,639,613 A | 6/1997 | Shay et al. |
| 6,664,046 B1 | 12/2003 | Chang et al. |
| 2006/0204956 A1 | 9/2006 | Kopreski et al. |
| 2010/0317000 A1 | 12/2010 | Zhu |

FOREIGN PATENT DOCUMENTS

| | | |
|---|---|---|
| WO | 2005049861 A2 | 6/2005 |
| WO | 2009115615 A2 | 9/2009 |

OTHER PUBLICATIONS

Horikawa, et al. (2005) "Differential cis-regulation of human versus mouse TERT gene expression in vivo: Identification of a human-specific repressive element", Proceedings of National Academy of Sciences, USA, 102(51): 18437-42.*
De Wilde, J. et al., "hTERT promoter activity and CpG methylation in HPV-induced carcinogenesis" BMC Cancer, 2010, 10:271.
Guilleret, I. et al., "Unusual distribution of DNA methylation within the hTERT CpG island in tissues and cell lines." Biochemical and Biophysical Research Communications, 2004, 325:1037-1043.
Widschwendter et al., "DNA Methylation in Serum and Tumors of Cervical Cancer Patients." Clinical Cancer Research, Feb. 3, 2004, 2004;10:565-571.
Zinn, R.L. et al., "hTERT is expressed in cancer cell lines despite promoter DNA methylation by preservation of unmethylated DNA and Active chromatin around the transcription stat site." Cancer Research, Jan. 1, 2007 (Jan. 1, 2007), 67(1):194-201 ISNN 0008-5472 see figures 1-3 and p. 198.
Castelo-Branco, P. et al., "Methylation of the TERT promoter and risk stratification of childhood brain tumours: an integrative genomic and molecular study." The Lancet Oncology, May 16, 2013, 14(6):534-542.
International Search Report and Written Opinion for related app. No. PCT/CA2013/000508, filed May 24, 2013, dated Aug. 27, 2013.

* cited by examiner

*Primary Examiner* — Robert M Kelly
(74) *Attorney, Agent, or Firm* — Benesch, Friedlander, Coplan & Aronoff, LLP; Thomas Y. Kendrick

(57) ABSTRACT

A method of diagnosing cancer in a mammal is provided. The method includes the steps of determining in a nucleic acid-containing sample from the mammal the degree of DNA methylation of a target region within the hTERT promoter from the nucleotide at about position −157 to the nucleotide at about position −580, or a corresponding target region in a TERT promoter in a mammal other than a human, to yield a sample methylation signature, determining the baseline degree of DNA methylation of the target region in a control sample to yield a control methylation signature, comparing the sample methylation signature to the control methylation signature and rendering a diagnosis of cancer when there is at least 1.5 times more methylation in the sample methylation signature as compared to the control methylation signature. Methods of determining tumor grade and progression, predicting survival and determining whether or not a mammal is a candidate for telomerase-targeted or demethylation therapy are also provided.

10 Claims, 27 Drawing Sheets
(1 of 27 Drawing Sheet(s) Filed in Color)

GCTGCGCAGCAGGGAGCGCACGGCTCGGCAGCGGGGAGCGCGCGGCATCGCGGGGGTGG
CCGGGGCCAGGGCTTCCCACGTGCGCAGCAGGACGCAGCGCTGCCTGAAACTCGCGCCGC
GAGGAGAGGGCGGGGCCGCGGAAAGGAAGGGGAGGGGCTGGGAGGGCCCGGAGGGGG
CTGGGCCGGGGACCCGGGAGGGGTCGGGACGGGGCGGGGTCCGCGCGGAGGAGGCGGA
GCTGGAAGGTGAAGGGGCAGGA<u>CGGGTGCCCGGGTCCCCAGTCCCTCCGCCACGTGGGAA</u>
<u>GCGCGGTCCTGGGCGTCTGTGCCCGCGAATCCACTGGGAGCCCGGCCTGGCCCCGACAGCG</u>
<u>CAGCTGCTCC</u>GGGCGGACCCGGGGGTCTGGGCCGCGCTTCCCCGCCCGCGCCGCTCGC
GCTCCCAGGGTGCAGGGACGCCAGCGAGGGCCCCAGCGGAGAGAGGTCGAATCGGCCTA
GGCTGTGGGGTAACCCGAGGGAGGGG*CCATGATGTGGAGGCCCTGGGAACAG<u>GTGCGTGC</u>*
*<u>GGCGACCCTTTGGCCGCTGGCCTGATCCGGAGA</u>CCAGGGCTGCCTCCAGGTCCGGACGCG*
*GGGCGTCGGGCTCCGGGCACCACGAATGCCGGACGTGAAGGGGAGGACGGAGGCGCGTA*
*GACGCGGCTGGGGACGAACCCGAGGACGCATTGCTC<u>CCTGGACGGGCACGCGGGACCTCCC</u>*
<u>GGAGTGCCTCCCTGCAACACTTCCCCGCGACTTGGGCTCCTTGACACAGGCCCGTCATTTCT</u>
<u>CTTTGCAGGTTCTCAGGCGGCGAGGGG</u>TCCCACCATGAGCAAACCACCCCAAATCTGTTAA
TCACCCACCGGGGCGGTCCCGTCGAGAAAGGGTGGGAAATGGAGCCAGGCGCTCCTGCTG
GCCGCGCACCGGGCGCCTCACACCAGCCACAACGGCCTTGACCCTGGGCCC
CGGCACTCTGTCTGGCAGATGAGGCCAACATCTGGTCACATCCCGCCCGC (SEQ ID NO: 1)

ATG (TAC) : position +78

GAG - Transcription start site

Region 1A – Location : -132 to -240

Region 1B – Location : -260 to -349

Region 2 – Location : - 402 to - 443

Region 3 – Location : - 566 to - 679

*Sequenom (italic)* - Location : -376 to -591

CG : CG or CpG site

FIGURE 1A

Methylation at CpG sites 1-25 within the hTERT Promotor

| Illumina | | 2,3 & | 5,6 & | | 10,11 | 13 & | 15 & | | 18,19 | | | 24 & | |
|---|---|---|---|---|---|---|---|---|---|---|---|---|---|
| PF SG | 1 | 4 | 7 | 8 & 9 & 12 | 14 | 16 | 17 | 20,21 | 22 | 23 | 25 | | |
| PF-A | 0.750 | 0.610 | 0.660 | 0.640 | 0.770 | 0.450 | 0.550 | 0.290 | 0.550 | 0.390 | 0.400 | 0.390 |
| PF-A | 0.660 | 0.470 | 0.520 | 0.400 | 0.510 | 0.320 | 0.500 | 0.170 | 0.370 | 0.210 | 0.240 | 0.200 |
| PF-A | 0.620 | 0.460 | NA | 0.360 | NA | 0.430 | 0.500 | 0.320 | 0.370 | 0.290 | 0.180 | 0.150 |
| PF-B | 0.070 | 0.070 | 0.070 | 0.100 | 0.110 | 0.030 | 0.390 | 0.020 | 0.130 | 0.080 | 0.040 | 0.120 |
| PF-B | 0.460 | 0.120 | 0.080 | 0.210 | NA | 0.070 | 0.370 | 0.030 | 0.250 | 0.100 | 0.000 | 0.180 |
| PF-B | 0.060 | 0.070 | 0.040 | 0.070 | 0.110 | 0.040 | 0.180 | 0.000 | 0.130 | 0.020 | 0.040 | 0.040 |

FIG. 2C

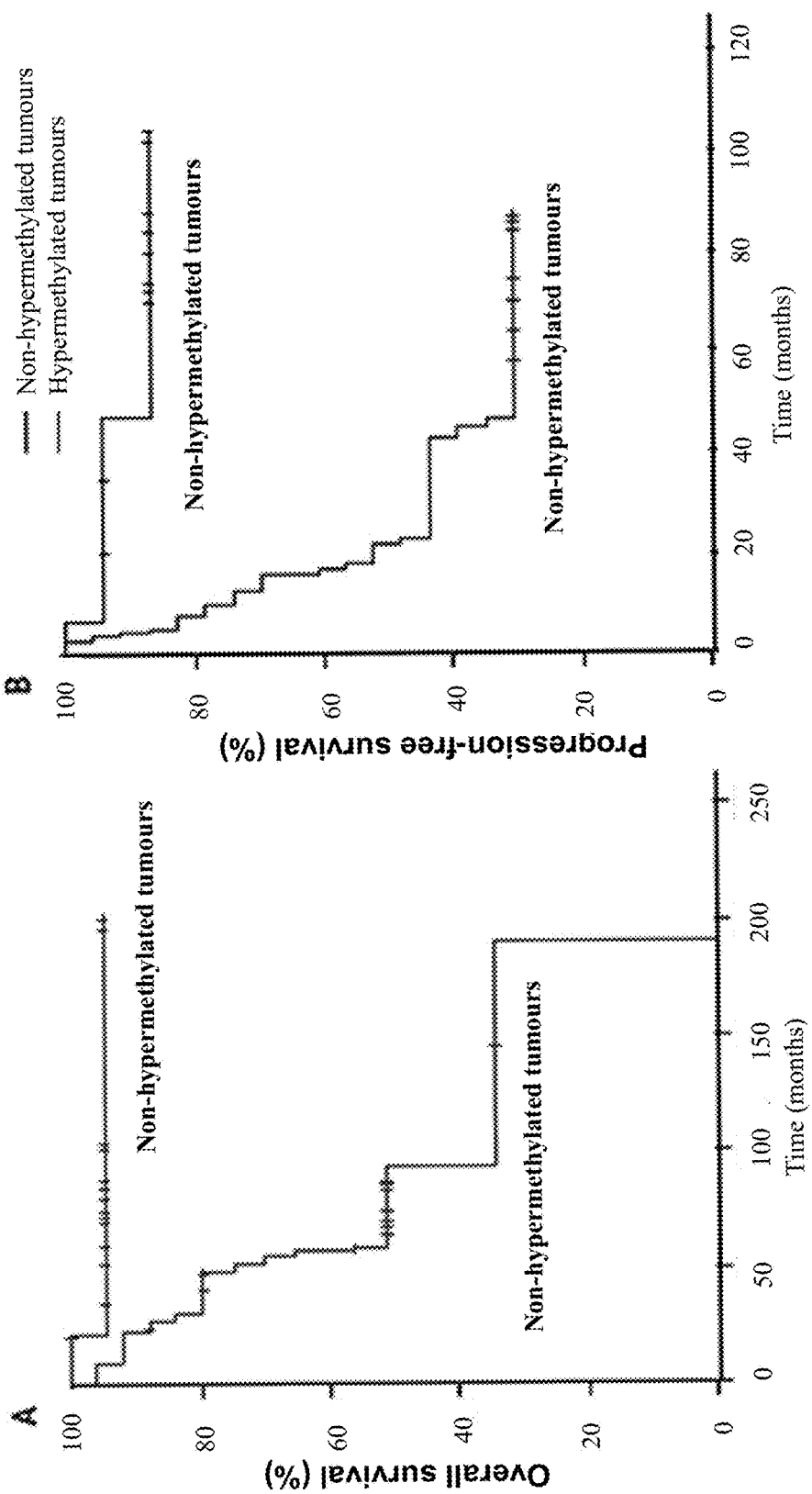

METHOD OF DIAGNOSING CANCER COMPRISING DETECTION OF THE METHYLATION SIGNATURE IN THE HTERT PROMOTER

FIELD OF THE INVENTION

The present invention relates generally to a method of diagnosing cancer as well as methods of prognosis and therapy.

SEQUENCE LISTING

Applicant incorporates by reference the sequence listing and all material in the associated sequence listing file, which is filed with this U.S. National Stage Entry. The sequence listing is included with this filing as "38174-3-sequence_listing.txt," which was created on Nov. 24, 2014, and which has a file size of 5,419 bytes.

BACKGROUND OF THE INVENTION

Telomeres are unique structures located at the ends of chromosomes. Their function is to prevent DNA ends from being recognized as DNA breaks which leads to activation of DNA repair mechanisms and results in cell growth arrest or death. During each cell replication cycle, a portion of the telomere is lost. Continued telomere shortening ultimately results in a growth-arrested state known as senescence or our molecular clock. Telomerase is an enzyme that elongates telomeric DNA, resulting in maintenance of telomeres and cellular immortality. Importantly, more than 85% of all malignant human cancers and almost 100% of advanced cancers express high levels of hTERT, the human catalytic subunit of telomerase.

hTERT expression has long been seen as a potential diagnostic or prognostic biomarker for cancer since activity is almost always high in cancer cells and low in normal cells. In many tumour types, the level of hTERT correlates with prognosis, and in other cases it can distinguish between malignant and benign lesions. Nevertheless, there are several flaws which make measurement of telomerase activity and/or hTERT expression difficult in the clinical setting. These include: 1) there is no reliable antibody for hTERT; 2) high-quality samples are required for accurate measurement of the entire hTERT complex (including the RNA and protein components of the enzyme) or RNA molecules, which are unstable and degradable; 3) clinical preparation of samples using formalin-fixation and paraffin-embedding (FFPE) further degrades RNA and, thus, the determination of TERT enzymatic activity and gene expression are unfeasible in most tumour samples; and 4) activated lymphocytes may have elevated hTERT expression contaminating the tumour tissue and producing false positive results. For these reasons, hTERT expression is currently not used as a clinical diagnostic and prognostic tool in cancer.

DNA methylation is the biochemical addition of a methyl group ($CH_3$) to a nucleotide molecule, which in adult mammals occurs predominantly to cytosines in cytosine-guanosine (CpG) dinucleotides. The promoter regions of most genes, including hTERT, contain CpG-rich regions known as CpG islands and DNA methylation is an epigenetic mechanism that can modulate expression of downstream genes. In most cases, promoter hypermethylation reduces gene expression. The hTERT promoter, however, is a large, complex promoter with a poorly understood methylation profile. Specifically, hypermethylation of the same promoter region occurs in both cancer and normal tissues and is associated with variable hTERT expression. In other regions of the promoter, there is hypomethylation in both cancer and normal tissue which is associated with variable hTERT expression.

It would be desirable, thus, to develop diagnostic and/or prognostic methods for cancer that overcome one or more of the disadvantages outlined above.

SUMMARY OF THE INVENTION

It has now been determined that DNA hypermethylation within a particular region in the TERT promoter is associated with cancer, while hypomethylation within this region is indicative of normal tissue, including benign low-grade tumours. This methylation signature is specific and effective for cancer diagnosis, prognostication and targeted therapies.

Thus, according to one aspect of the invention, a method of diagnosing cancer in a mammal is provided comprising the steps of determining in a nucleic acid-containing sample from the mammal the degree of DNA methylation of a target region within the hTERT promoter from the nucleotide at about position −157 to the nucleotide at about position −580, or a corresponding target region within a TERT promoter in a mammal other than a human, to yield a sample methylation signature, determining the baseline degree of DNA methylation in the target region in a control sample to yield a control methylation signature, comparing the sample methylation signature to the control methylation signature and rendering a diagnosis of cancer when there is at least 1.5 times more methylation in the sample methylation signature as compared to the control methylation signature.

In another aspect of the invention, a method of predicting survival in a mammal with cancer is provided comprising the steps of determining in a nucleic acid-containing sample from the mammal the degree of DNA methylation of a target region within the hTERT promoter from the nucleotide at about position −157 to the nucleotide at about position −580, or a corresponding target region within a TERT promoter in a mammal other than a human, to yield a sample methylation signature, determining the baseline degree of DNA methylation in the target region in a control sample to yield a control methylation signature, and comparing the sample methylation signature to the control methylation signature. A prediction of overall or progression-free survival may be rendered when there is at least 1.5 times more methylation in the sample methylation signature as compared to the control methylation signature.

In a further aspect of the invention, a method of predicting tumour progression in a mammal with a tumour is provided comprising the steps of determining in a tumour sample from the mammal the degree of DNA methylation of a target region within the hTERT promoter from the nucleotide at about position −157 to the nucleotide at about position −580, or in a corresponding target region in a TERT promoter in a mammal other than a human, to yield a sample methylation signature, determining the baseline degree of DNA methylation in the target region in a control sample to yield a control methylation signature, comparing the sample methylation signature to the control methylation signature and predicting that the tumour will progress in the mammal when there is at least 1.5 times more methylation in the sample methylation signature as compared to the control methylation signature.

In another aspect, a method of identifying the grade of a tumour in a mammal is provided comprising the steps of determining in a tumour sample from the mammal the degree of DNA methylation of a target region within the hTERT promoter from the nucleotide at about position −157 to the nucleotide at about position −580, or a corresponding target region in a TERT promoter in a mammal other than a human, to yield a sample methylation signature, determining the baseline degree of DNA methylation in the target region in a control sample to yield a control methylation signature, comparing the sample methylation signature to the control methylation signature and identifying a tumour be a malignant tumour when there is at least 1.5 times more methylation in the sample methylation signature as compared to the control methylation signature.

In yet another aspect, a method of determining whether or not a mammal with cancer is a candidate for treatment with a telomerase-targeted or demethylation therapy is provided comprising the steps of determining in a nucleic acid-containing sample from the mammal the degree of DNA methylation of a target region within the hTERT promoter from the nucleotide at about position −157 to the nucleotide at about position −580, or a corresponding target region in a TERT promoter in a mammal other than a human, to yield a sample methylation signature, determining the baseline degree of DNA methylation within the target region in a control sample to yield a control methylation signature, comparing the sample methylation signature to the control methylation signature and deducing that the mammal is a candidate for telomerase-targeted or demethylation therapy when there is at least 1.5 times more methylation in the sample methylation signature as compared to the control methylation signature.

These and other aspects of the invention are described in the detailed description and examples that follow with reference to the following figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 8 graphically illustrates that methylation status in region 2 of hTERT is predictive of over-all survival (A) and progression-free survival (B) in ependymoma patients;

DETAILED DESCRIPTION OF THE INVENTION

Figure 1B:
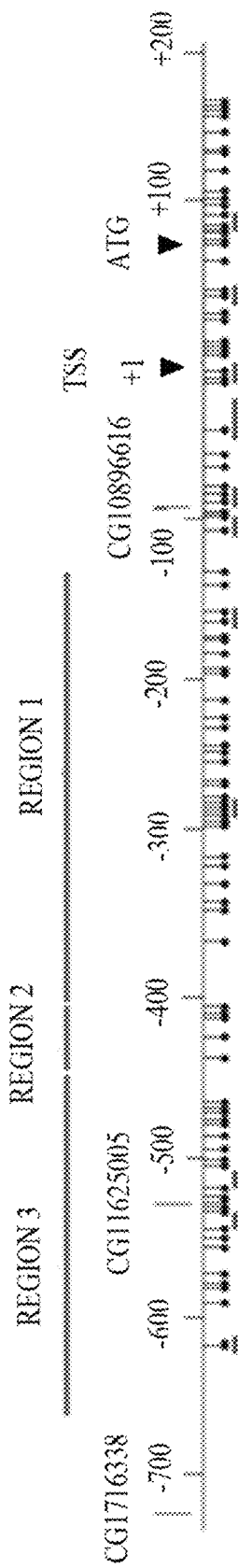
FIG. 1 illustrates the nucleotide sequence of the proximal hTERT promoter showing the regions used for Sequenom® and pyrosequencing (A), as well as a schematic representation of the proximal hTERT promoter showing the probes used for Illumina methylation array and regions used for pyrosequencing (B)

The invention relates, in one of its aspects, to a method of diagnosing cancer in a mammal. The method comprises the steps of determining in a nucleic acid-containing sample from the mammal the degree of DNA methylation of a target region within the hTERT promoter from the nucleotide at about position −157 to the nucleotide at about position −580, or in a corresponding target region in a TERT promoter in a mammal other than a human, to yield a sample methylation signature, determining the baseline degree of DNA methylation within the target region in a control sample to yield a control methylation signature, comparing the sample methylation signature to the control methylation signature and rendering a diagnosis of cancer when there is at least 1.5 times more methylation in the sample methylation signature as compared to the control methylation signature.

The term "TERT" is used herein to refer to mammalian telomerase reverse transcriptase, including human (hTERT) and non-human TERT.

The term "TERT promoter" refers to the region upstream of the transcription start site of the gene encoding TERT, i.e. the TERT gene, namely, the region upstream of the transcription start site beginning at position −1 and extending upstream therefrom, in particular, nucleotides in the proximal region of the promoter spanning from position −1 to about −1000. FIG. 1A illustrates the nucleotide sequence of the proximal region of the TERT promoter.

The term "cancer" is used herein to encompass cancers that can express TERT. Such cancers include, but are not limited to, carcinoma such as bladder, breast, colon, kidney, brain, liver, lung, including small cell lung cancer, esophagus, gall-bladder, ovary, pancreas, stomach, cervix, thyroid, prostate, and skin, including squamous cell carcinoma; sarcomas; malignant neoplasms; hematopoietic tumours of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumours of myeloid lineage including acute and chronic myelogenous leukemias, myelodysplastic syndrome and promyelocytic leukaemia; tumours of mesenchymal origin, including fibrosarcoma and rhabdomyosarcoma; tumours of the central and peripheral nervous system, including astrocytoma neuroblastoma, glioma and schwannomas; other tumours, including melanoma, seminoma, teratocarcinoma, osteosarcoma, xeroderma pigmentosum, keratoxanthoma, thyroid follicular cancer, Kaposi's sarcoma and pediatric cancers from embryonal and other origins.

The term "mammal" is used herein to encompass mammals in which telomerase is not ubiquitously expressed. Such mammals include, for example, humans, cats, dogs, horses, cattle, pigs and various wild animals. Mice, and any other mammal in which telomerase is ubiquitously expressed, are not included within this definition.

In the present method, analysis of the DNA methylation signature of the TERT promoter is conducted on a biological nucleic acid-containing sample, preferably a patient-derived primary biological sample, including for example, blood, serum, plasma, urine, biopsied tissue including but not limited to tumour tissue, or pleural effusions obtained from a mammal. The sample may be obtained using techniques well-established and known to those of skill in the art, and will vary depending on the sample type as one of skill in the art will appreciate. Examples of different techniques that may be used to obtain a tumour sample include standard biopsy, needle biopsy, endoscopic biopsy, bone marrow biopsy, and combination techniques which employ biopsy and imaging techniques. Needle biopsy is commonly used to obtain a sample from a tumour under the skin surface, e.g. breast tumour. A sample of a brain tumour may be obtained by standard biopsy, stereotactic biopsy or neuroendoscopy. Generally, a suitable tumour sample will contain up to about 1 µg, typically, in the range of about 50 ng-1 µg of nucleic acid to be useful to determine methylation within the target region of the TERT promoter.

Nucleic acid from the tumour sample may be extracted from the sample using techniques well-known to those of skill in the art, including chemical extraction techniques utilizing phenol-chloroform (Sambrook et al., 1989), guanidine-containing solutions, or CTAB-containing buffers. As well, as a matter of convenience, commercial DNA extraction kits are also widely available from laboratory reagent supply companies, including for example, the QIAamp DNA Blood Minikit available from QIAGEN® (Chatsworth, Calif.), or the Extract-N-Amp blood kit available from Sigma-Aldrich® (St. Louis, Mo.).

Once an appropriate nucleic acid sample is obtained, the degree of methylation in a target region within the TERT promoter from the nucleotide at about position −157 to the nucleotide at about position −580 of the TERT promoter, i.e. at chromosome 5:1,295,338-1,295,791 (GRCh37/hg19, in other words, nucleotides 1,295,338-1,295,791 on chromosome 5 of the human genome $19^{th}$ assembly is determined. The term "degree of methylation" is used herein to refer to extent to which there is methylation at CG sites, or the methylation signature or methylation status, of a target region within the portion of the TERT promoter from the nucleotide at about position −157 to the nucleotide at about position −580. Methylation of a target region including any number of CG sites within this portion of the TERT promoter may be determined for comparison to a control, including 1 CG site to multiple CG sites. CG sites within the target region may or may not be contiguous CG sites within this portion of the TERT promoter. Preferably, methylation of at least about 2 CG sites, and more preferably at least about 3 or more CG sites is determined, up to all or a majority of detectable CG sites (depending on the technique used to identify CG sites, the number of detectable CG sites may vary) that are within the TERT promoter portion of nucleotide −157 to nucleotide −580. In addition, it is preferred that the CG sites be contiguous.

In order to determine the degree of methylation at CG sites within a target region of the TERT promoter (as shown in FIG. 1A), the target region is bisulfite converted using standard kits for this purpose, amplified using well-established methods including PCR, and the degree of methylation at CG sites in the region is then determined using known techniques such as pyrosequencing or Sequenom® analysis.

The degree of methylation of CG sites within the same target region of the TERT promoter is similarly determined using an appropriate technique in a corresponding control or normal biological sample. A control or normal biological sample is a non-cancerous sample of a corresponding biological sample from the same mammal or from a mammal determined to be comparable, e.g. in the case of a test sample from a human, a control sample may be obtained from another human, that may or may not be of the same age or sex. Generally a median value of methylation determined within the target TERT promoter region from multiple control samples aids in providing an accurate control value. In this regard, it is noted that normal biological samples exhibit a small degree or baseline amount of methylation that may vary from sample type to sample type. Thus, the determination of the degree of methylation in a target TERT region of a control sample assists in providing an accurate analysis of the actual methylation degree in a test sample, i.e. whether or not hypermethylation actually exists in the test sample being analyzed.

To render a diagnosis of cancer, the degree of methylation in the target region of the TERT promoter within a selected biological sample is then compared to a control degree of methylation, and the difference in the degree of methylation in the target region of the TERT promoter in a sample and the degree of methylation in the control is determined. A determination of an increased degree of methylation in the target region of the TERT promoter of at least about 1.5 fold, preferably at least about 2 fold, and more preferably at least about 3 fold, in comparison to the degree of methylation in the control is referred to herein as hypermethylation and such hypermethylation indicates that the mammal has cancer.

Alternatively, in the absence of determining the degree of methylation in a control, the degree of methylation in normal (non-cancerous) tissue is known to generally be within the range of about 1-10%. Thus, a determination of a degree of methylation in the TERT promoter target region of a sample of at least about 15% or greater methylation, e.g. preferably at least about 20%, is indicative of hypermethylation in the target region. Such hypermethylation indicates that the sample is a cancerous sample, and thus, that the mammal from which the sample was obtained has cancer.

In another aspect of the invention, a method of predicting survival, including overall survival and progression-free survival, in a mammal with cancer is provided. As one of skill in the art will appreciate, the term "overall survival" within a given period of time (generally years) refers to the percentage of those diagnosed with the same cancer that survived for the given period of time following their diagnosis, either with or without treatment. Thus, 5 year overall survival is the percentage of those diagnosed with the same cancer that survived for at least 5 years after their diagnosis. The term "progression-free survival" within a given period of time (generally years) refers to the percentage of those diagnosed with the same cancer whose cancer did not progress for the given period of time following their diagnosis, either with or without treatment. This method comprises the steps of determining in a nucleic acid-containing sample from the mammal the degree of DNA methylation of a target region within the hTERT promoter from the nucleotide at about position −157 to the nucleotide at about position −580, or a corresponding target region in a TERT promoter in a mammal other than a human, to yield a sample methylation signature, determining the baseline degree of DNA methylation of the target region in a control sample to yield a control methylation signature, and comparing the sample methylation signature to the control methylation signature. In this case, the control may be a normal baseline value, or may be a previous sample from the patient (e.g. prior to treatment) while the sample may be taken subsequent to treatment. A prediction of overall or progression-free survival may be rendered when there is at least 1.5 times more methylation in the sample methylation signature as compared to the control methylation signature. In one embodiment, a prediction that overall or progression-free survival is less than 50% may be rendered when there is at least 1.5 times more methylation, preferably 2 times more methylation and more preferably at least about 3 times more methylation, in the sample methylation signature as compared to the control methylation signature, for example, a prediction that 5-10 year overall or progression-free survival is less than 50%, including less than 10-30%, may be rendered when there is at least 1.5 times more methylation in the sample methylation signature as compared to the control methylation signature.

In another aspect, a method of predicting tumour progression in a mammal with a tumour is provided. The term "tumour progression" is meant to refer to the advancement of a tumour from a low-grade, benign state to a high-grade, malignant state. For clarity, malignant cells are those cells that exhibit multiple characteristics selected from the group consisting of uncontrolled proliferation, evading growth suppressors, avoiding cell death, limitless proliferative capacity (immortality), metastatic capacity and genetic instability. Details of cancer cell properties are described in Hanahan et al. Cell (2011) 144: 646-674, the contents of which are incorporated herein by reference. The method comprises the steps of determining in a tumour sample from the mammal the degree of DNA methylation of a target region within the hTERT promoter from the nucleotide at about position −157 to the nucleotide at about position −580, or a corresponding target region in a TERT promoter in a mammal other than a human, to yield a sample methylation signature, determining the baseline degree of DNA methylation of the target region in a control sample, e.g. a previous tumour sample from the mammal, to yield a control methylation signature, and comparing the sample methylation signature to the control methylation signature. If sample methylation signature exhibits hypermethylation in comparison to the control methylation signature, e.g. at least 1.5 times more methylation in the sample, preferably 2 times more methylation and more preferably at least about 3 times more methylation, methylation signature as compared to the control methylation signature, then it is predicted that the tumour will progress from a low-grade benign tumour to a high-grade malignant tumour.

The term "low grade tumour" in a mammal is used herein to refer to a tumour that does not progress to result in death of the mammal, e.g. a benign tumour. A benign tumour may be a premalignant tumour. On the other hand, a "high grade tumour" in a mammal is used herein to refer to a tumour that progresses to result in death of the mammal, e.g. a malignant tumour.

Similarly, in a further aspect, a method of identifying tumour grade of a tumour within a mammal is provided. The method comprises the steps of determining in a tumour sample from the mammal the degree of DNA methylation of a target region within the hTERT promoter from the nucleotide at about position −157 to the nucleotide at about position −580, or a corresponding target region in a TERT promoter in a mammal other than human, to yield a sample methylation signature, determining the baseline degree of DNA methylation of the target region in a control sample, e.g. a normal sample, to yield a control methylation signature, and comparing the sample methylation signature to the control methylation signature. A tumour is identified to be a malignant tumour, as opposed to a benign tumour, when there is at least 1.5 times more methylation, preferably at least 2-3 times more methylation, in the sample methylation signature as compared to the control methylation signature.

A method of determining whether or not a mammal with cancer is a candidate for treatment with a telomerase-targeted or demethylation therapy is also provided. The method comprises the steps of determining in a nucleic acid-containing sample from the mammal the degree of DNA methylation of a target region within the hTERT promoter from the nucleotide at about position −157 to the nucleotide at about position −580, or a corresponding target region in a TERT promoter in a mammal other than a human, to yield a sample methylation signature, determining the baseline degree of DNA methylation of the target region in a control sample, e.g. a normal sample, to yield a control methylation signature, and comparing the sample methylation signature to the control methylation signature. Based on an analysis of the results obtained, it may then be determined whether or not the mammal is a candidate for treatment with telomerase-targeted therapy, modulators of TERT or demethylation therapy. When an analysis of the results indicates that there is hypermethylation of the target region of the TERT promoter (i.e. there is at least 1.5 times more methylation in the sample methylation signature as compared to the control methylation signature), then it is determined that the mammal is a candidate for treatment with a telomerase-targeted or demethylation therapy. On the other hand, if there is no such hypermethylation, then the mammal is not a candidate for treatment with a telomerase-targeted or demethylation therapy.

Telomerase-targeted therapy includes therapies by which telomerase is inhibited, including small molecule inhibitors such as Imetelstat and telomestatin and any other telomerase inhibitor. Demethylation therapy includes any demethylation agent, including but not limited to, 5 azacytidine (VIDAZA) and derivatives thereof such as 5-aza-2'-deoxycytidine (DECITABINE).

In a further aspect, a method of characterizing a malignant tumour obtained from a mammal is provided. This method comprises determining in a sample of the tumour the degree of DNA methylation of a target region within the hTERT promoter from the nucleotide at about position −157 to the nucleotide at about position −580, or within a corresponding target region in a TERT promoter in a mammal other than a human, to yield a sample methylation signature, determining the baseline degree of DNA methylation of the target region in a control sample to yield a control methylation signature, comparing the sample methylation signature to the control methylation signature and deducing that the tumour is an alternative lengthening of telomeres phenotype when there is no significant difference in methylation between the sample and control methylation signatures, e.g. less than about 1.5 times more methylation in the sample methylation signature as compared to the control methylation signature, or no substantial increase in methylation in the sample methylation signature.

All references referred to herein are incorporated by reference.

Embodiments of the invention are described in the following specific example which is not to be construed as limiting.

Example—Determination of DNA Methylation Signature in hTERT

Methods and Materials
RT-PCR.

Total RNA was extracted from several different tissues or cell lines using Trizol reagent (Invitrogen) and 500 ng of total RNA was reverse transcribed with Superscript II (Invitrogen). The RT-PCR reaction was carried out with 60 ng of cDNA, 10 μM of hTERT forward (TGA CAC CTC ACC TCA CCC AC (SEQ ID NO: 2)) and reverse (CAC TGT CTT CCG CAA GTT CAC (SEQ ID NO: 3)) primers, and 1×CYBR green mix (Roche). PCR analyses were performed on a LightCycler 480 (Roche) after 40 cycles (95° C., 15"; 60° C., 40"; 72° C., 15"). The hTERT expression levels of the different tissues and cell lines were normalized to hTERT levels observed in Hela cells.

Patient Tissues and Cell Lines.

Samples were obtained with patients' consent according to the Research Ethics Boards at The Hospital for Sick Children and Toronto Western Hospital. Fetal Neural Stem (NS) HF240 cells, human Mesenchymal Progenitor cells, human umbilical cord perivascular cells, and human skin-derived precursors hSKPs were previously described (Castelo-Branco et al. Clin Cancer Res. 2011 Jan. 1; 17(1): 111-21). Glioma tumour-initiating cell (TIC) lines G179 and GLINS1 were derived from patients diagnosed with classic glioblastoma multiforme and maintained as previously described (Castelo-Branco et al., 2011). All cell lines and patient samples are described in Table 1.

TABLE 1

| | Comments |
|---|---|
| Normal Tissue (n = 60) | |
| Embryonic stem cells (n = 2) | |
| Tissue stem cells (n = 6) | Neural Stem, Mesenchymal, skin-derived progenitors. |

TABLE 1-continued

| | Comments |
|---|---|
| Haematopoietic stem cells (n = 6) | Cord blood |
| IPS, IPS Differentiated cells (n = 4) | Skin |
| Blood (n = 19) | Blood |
| Fibroblasts (n = 2) | Skin |
| Normal Brain (n = 7) | Brain |
| Placenta (n = 14) | |
| Prostate (n = 25) | Prostate |
| Cancer cell lines (24) | |
| HeLa | Cervical cancer |
| RH6, A204 | Embryonic rhabdomyosarcoma |
| H1299 | Adrenocortical carcinoma |
| HepG2 | Hepatic carcinoma |
| Med8, UW228, ONS70 | Medulloblastoma |
| U87, U118, LN229, A117, LN18 | Glioblastoma |
| SK-N-Be2, IMR5, CHLA15, CHLA 90, SK-N-AS, NGP, CHLA20 | Neuroblastoma |
| GliNS, G179, G414, TB1 | Brain tumour initiating cell lines |
| Tumours (around 464) | |
| Pediatric low grade gliomas (n = 80) | Brain |
| Adult low grade gliomas (n = 8) | Brain |
| Choroid plexus papillomas (n = 19) | Brain |
| Atypical Choroid plexus papillomas (n = 8) | Brain |
| Choroid plexus carcinomas (n = 19) | Brain |
| Oligodendro/astrogliomas (n = 9) | Brain |
| Diffuse pontine gliomas (n = 10) | Brain |
| Adult High Grade Gliomas (n = 34) | Brain |
| Ependymomas (n = 79) | Brain |
| Leukemias (n = 13) | Blood |
| Adrenocortical Carcinomas (n = 8) | Adrenal gland |
| Medulloblastomas (n = 106) | Brain |
| Colon cancer (n = 10) | Colon |
| Atypical teratoid rhabdoid tumour (n = 36) | Brain |
| Prostate cancer (n = 25) | Prostate |

Statistical Analysis.

Analyses were done with GraphPad Prism v. 4 (San Diego, Calif.) and SPSS v15.

Sequenom® and pyrosequencing methods were used to determine the degree of methylation at CG sites within the proximal region of hTERT in normal tissues, and in various cancer cell lines and tumours.

Illumina® Methylation Array

Methylation within the hTERT promoter was assessed using the HumanMethylation450k BeadChip (Illumina®, San Diego, USA). The array comprised 3 sites located within the core promoter area, namely, cg 11625005 (at nucleotide position −555), cg17166338 (at nucleotide position −787) and cg10896616 (at nucleotide position −85). Methylation analysis was performed according to the manufacturer's instructions at the DKFZ Genomics and Proteomics Core Facility (Heidelberg, Germany). Methylation analysis was performed using the following filtering criteria: removal of probes targeting the X and Y chromosomes (n=11,551), removal of probes containing a single-nucleotide polymorphism (dbSNP132 Common) within five base pairs of and including the targeted CpG-site (n=24,536), and probes not mapping uniquely to the human reference genome (hg19) allowing for one mismatch (n=9,993). In total 438,370 probes were kept for analysis. The beta values were converted to z-scores by subtracting the mean beta value and dividing by the standard deviation. These values were then visualized in a heatmap indicating decreased DNA methylation and increased DNA methylation.

Sequenom® Analysis

Sequenom® analysis of hTERT was performed at McGill University and Genome Québec Innovation Centre as previously described (Coolen et al, Nucleic Acids Research, 2007, 1-14) using the hTERT forward aggaagagagGGGAAGTGTTGTAGGGAGGTATTT (SEQ ID NO: 4) and reverse cagtaatacgactcactatagggagaaggctAAAAC-CATAATATAAAAACCCTAAA (SEQ ID NO: 5) primers. The amplicon, as shown below, comprised 25 CpG informative sites (shown in bold below) within nucleotides at positions −376 to −591 of the promoter located at: Human Genome 19 assembly—chr5:1,295,557-1,295,772 (GRCh37/hg19).

(SEQ ID NO: 6)
CCATGATGTGGAGGCCCTGGGAACAGGTGCGTGCGGCGACCCTTTGGCCG

CTGGCCTGATCCGGAGACCCAGGGCTGCCTCCAGGTCCGGACGCGGGGCG

TCGGGCTCCGGGCACCACGAATGCCGGACGTGAAGGGGAGGACGGAGGCG

CGTAGACGCGGCTGGGGACGAACCCGAGGACGCATTGCTCCCTGGACGGG

CACGCGGGACCTCCCG.

Pyrosequencing Analysis:

Quantitative sodium bisulfite pyrosequencing was performed on various hTERT promoter regions as follows. Genomic DNA (50 ng to 1 ug) was sodium bisulfite modified using EpiTect Bisulfite kit (Qiagen®). Sodium bisulfite modified genomic DNA was then amplified using Hot-Start Taq master mix (Qiagen®) as previously described (Guo et al. Dev Biol. 2008 Aug. 1; 320(1):79-91). Regions of interest were amplified by PCR and pyrosequencing was carried out using the PyroMark Q24 pyrosequencer (Qiagen®) according to the manufacturer's protocol (Pyro-Gold reagents). Output data were analyzed using PyroMark Q24 1.0.10 Software (Qiagen®), which calculates the methylation percentage (mC/(mC+C)) for each CpG site, allowing quantitative comparisons.

Quantitative sodium bisulfate pyrosequencing was performed on region 1 of the hTERT promoter. Methylation of the following regions, 1A and 1B, was determined using pyrosequencing: CGGGTGCCCGGGTCCCCAGTC-CCTCCGCCACGTGGGAAGCGCGGTC-CTGGGCGTCTGTGCCC GCGAATCCACTGGGAGC-CCGGGCCTGGCCCCGACAGCGCAGCTGCTCC (SEQ ID NO: 7) (nucleotide positions −132 to −240 located at Human Genome 19 assembly—Chromosome 5:1,295,313-1,295,421; and GGCCGCGCTTCCCCGCCCGCGCGC-CGCTCGCGCTCCCAGGGTGCAGGGACGCCAGC-GAGGG CCCCAGCGGAGAGAGGTCGAATCGGCCTA (SEQ ID NO: 8) (nucleotide positions −260 to −349 located at Human Genome 19 assembly—Chromosome 5:1,295, 441-1,295,530 (GRCh37/hg19). PCR primers used were as follows: forward, TTGGAAGGTGAAGGGGTAG (SEQ ID NO: 9) and reverse TATGATGTGGAGGTTTTGGG (SEQ ID NO: 10), and for pyrosequencing GGTGAAGGGG-TAGGA (SEQ ID NO: 11) and GGATTAGGGGGTTTG (SEQ ID NO: 12) primers were used. The amplicon was 286 bp including the primers.

Methylation using pyrosequencing was also determined on the following region 2: GTGCGTGCGGCGAC-CCTTTGGCCGCTGGCCTGATCCGGAGAC (SEQ ID NO: 13) (nucleotide positions −402 to −443) located at the following coordinates: Human Genome 19 assembly—Chromosome 5:1,295,583-1,295,624 (GRCh37/hg19). The PCR primers used were as follows: forward—ATGATGTG-GAGGTTTTGGGAATAG (SEQ ID NO: 14) and reverse—CCCAACCTAAAAACAACCCTAAAT (SEQ ID NO: 15) and for pyrosequencing—GGAGGTTTTGGGAATAG (SEQ ID NO: 16). The PCR amplicon was 88 bp (including primers).

Methylation using pyrosequencing was also determined on the following region 3: CCTG-GACGGGCACGCGGGACCTCCCGGAGTGCCTCCCT-GCAACACTT CCCCGCGACTTGGGCTCCTT-GACACAGGCCCGTCATTTCTCTTTGCAGGTTCTCAGGC GGCGAGGGG (SEQ ID NO: 17) (nucleotide positions −566 to −679) with the following coordinates: Human Genome 19 assembly—Chromosome 5:1,295,747-1,295, 860 (GRCh37/hg19). The PCR primers used were as follows: forward—GGTTTGATTYGGAGATTTAGGGTT-GTTT (SEQ ID NO: 18) and reverse—AGAAAGGGTGGGAAATGGA (SEQ ID NO: 19) and for pyrosequencing—GAGGAAGTATTGTTT (SEQ ID NO: 20). The PCR amplicon was 330 bp (including primers).

Demethylation:

To determine the effect of demethylation of a target region of the TERT promoter, namely the hTERT region including nucleotides at positions −402 to −443, cells were treated with 20 µM 5-AZA 5 (Azacytidine) for 72 hours in combination with 600 nm TSA (Trichostatin A) for 18 hours.

Telomerase Inhibition

HF240 normal neural stem cell line and the G179 TIC line were treated twice a week with 5 µM Imetelstat telomerase inhibitor. Cell population doubling analysis after treatment was then determined.

Results

The proximal region of the hTERT promoter is shown in FIG. 1A, showing the regions used for Sequenom and pyrosequencing, and illustrating the CG sites (bolded) therein. The Illumina® Infinium HumanMethylation450 array covers the area with probes Cg17166338, Cg11625005 and Cg10896616, namely, at nucleotides at positions −85, −555 and −787, respectively, as shown in FIG. 1B.

Illumina Methylation Array

Figure 2A:
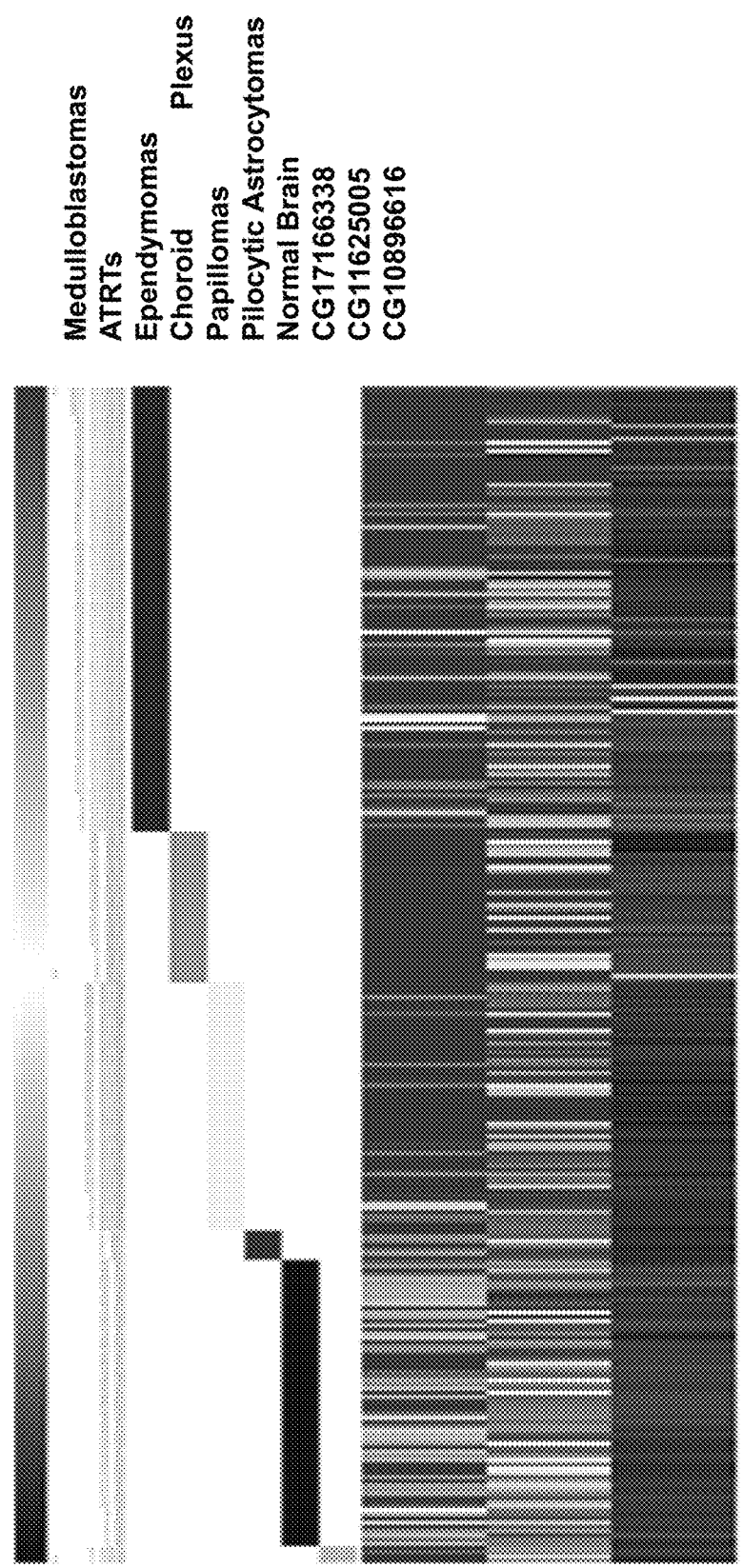
FIG. 2 illustrates the differential methylation determined using the Illumina® human methylation array within the hTERT promoter in normal brain vs brain tumour samples (A), and Sequenom® analysis of 25 CG sites with nucleotides at positions −376 to −591 of the hTERT promoter showing hypermethylation in tumour samples (PF-A) and hypomethylation in normal tissue samples (PF-B) (B)
FIG. 2C illustrates in tabular form Sequenom® analysis of the 25 CG sites within region 2 of the hTERT promotor as shown in FIG. 2B.

As shown in FIG. 2A, the hTERT promoter is differentially methylated in normal versus tumour samples. Human-Methylation450 array analysis of 4 normal brain tissue samples and 298 pediatric brain tumour samples show specific methylation (red) for malignant tumours (ependymomas, atypical teratoid rhabdoid tumours and medulloblastomas) at the Cg11625005 site. Low methylation (blue) was observed in normal tissue, pilocytic astrocytomas and choroid plexus papillomas at the same site. Cg17166338 is always methylated and Cg10896616 is always non-methylated in both normal and malignant samples.

Sequenom® Analysis

Figure 2B:
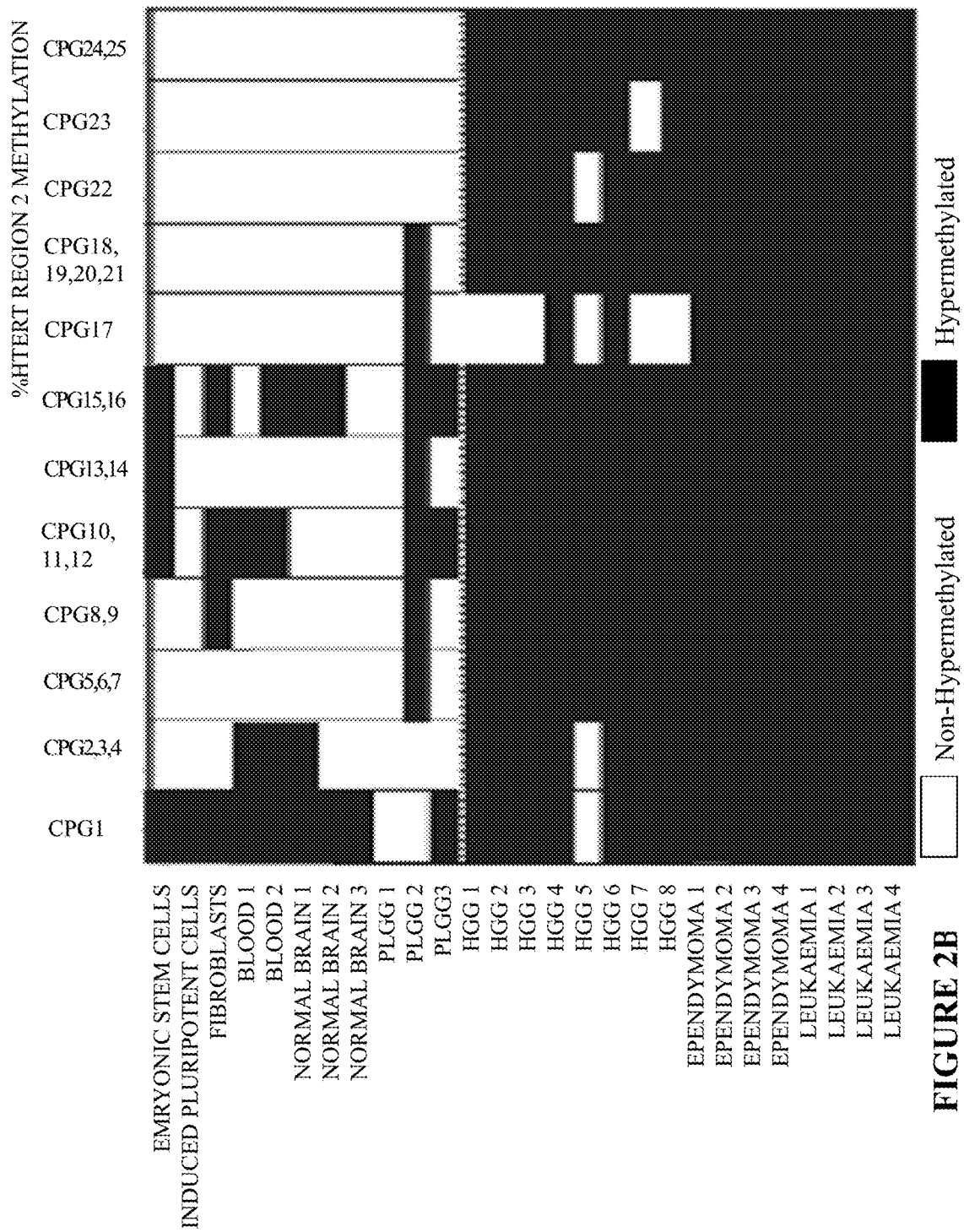

Sequenom® analysis of the 25 CG sites within region 2 of the hTERT promotor revealed, as shown in FIG. 2B and FIG. 2C, that tumour samples (PF-A) are hypermethylated across this region (as shown in bold) whereas normal tissue samples (PF-B) show hypomethylation within this region (as shown in italics). CG site number 5 in the Sequenom analysis corresponds to the Cg11625005 in the Infinium HumanMethylation450™ array. Region 2 comprises sites 21 through 25 and was chosen for pyrosequencing analysis.

Pyrosequencing Analysis

Figure 3A:
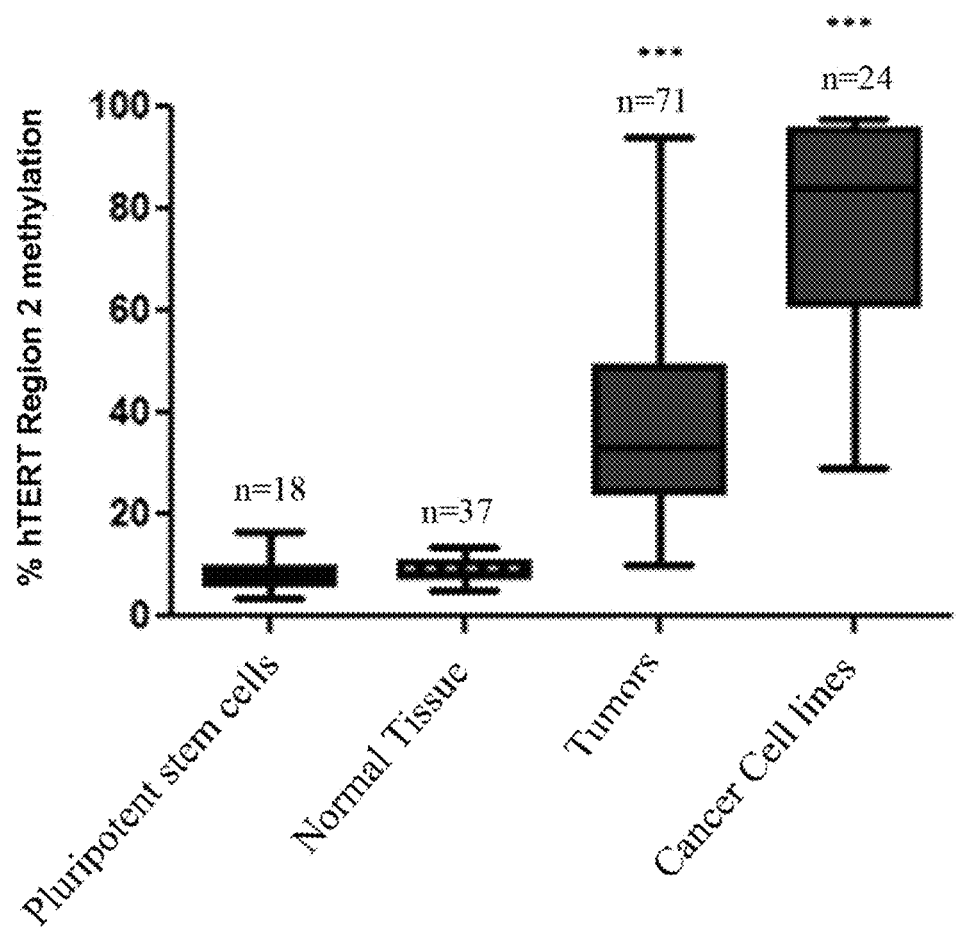
FIG. 3 graphically illustrates pyrosequencing results showing that hypermethylation in region 2 of hTERT-expressing tumour tissue and tumour cell lines as compared to normal tissue and pluripotent stem cells, respectively (A), a graph providing a comparison of the degree of methylation across about 40 CG sites within the hTERT promoter in tumour and normal tissues (B), a graph illustrating the degree of methylation within a subsection of region 1 of hTERT in tumour and normal brain tissue (C), and a graph illustrating the degree of methylation in region 2 of hTERT in tumour and normal prostate tissue (D)

Pyrosequencing analysis of region 2 shows no methylation in any normal tissue analysed including embryonic stem cells, tissue stem cells and iPS cells. However, significant hypermethylation of region 2 was observed in patient derived tumours samples (high grade gliomas, leukemias and colon cancer) (P<0.0001) and cancer cell lines (cancer and tumour-initiating cell lines) (P<0.0001) when compared to normal tissue samples as shown in FIG. 3A.

Figure 3B:
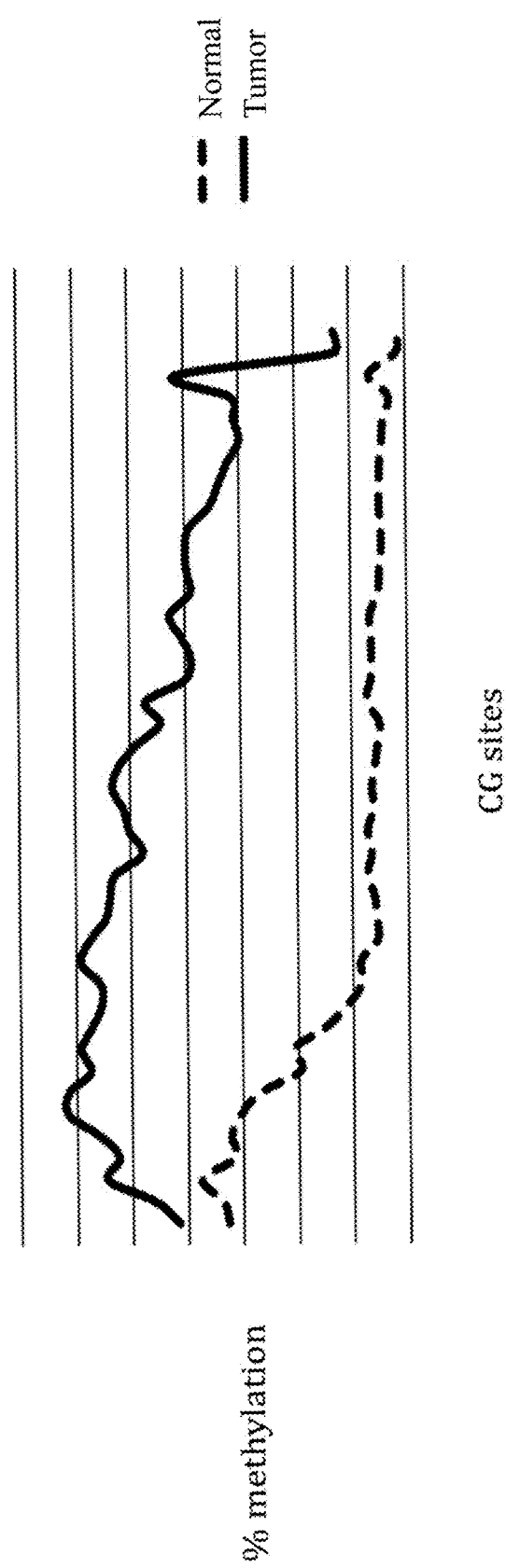
Figure 3C:
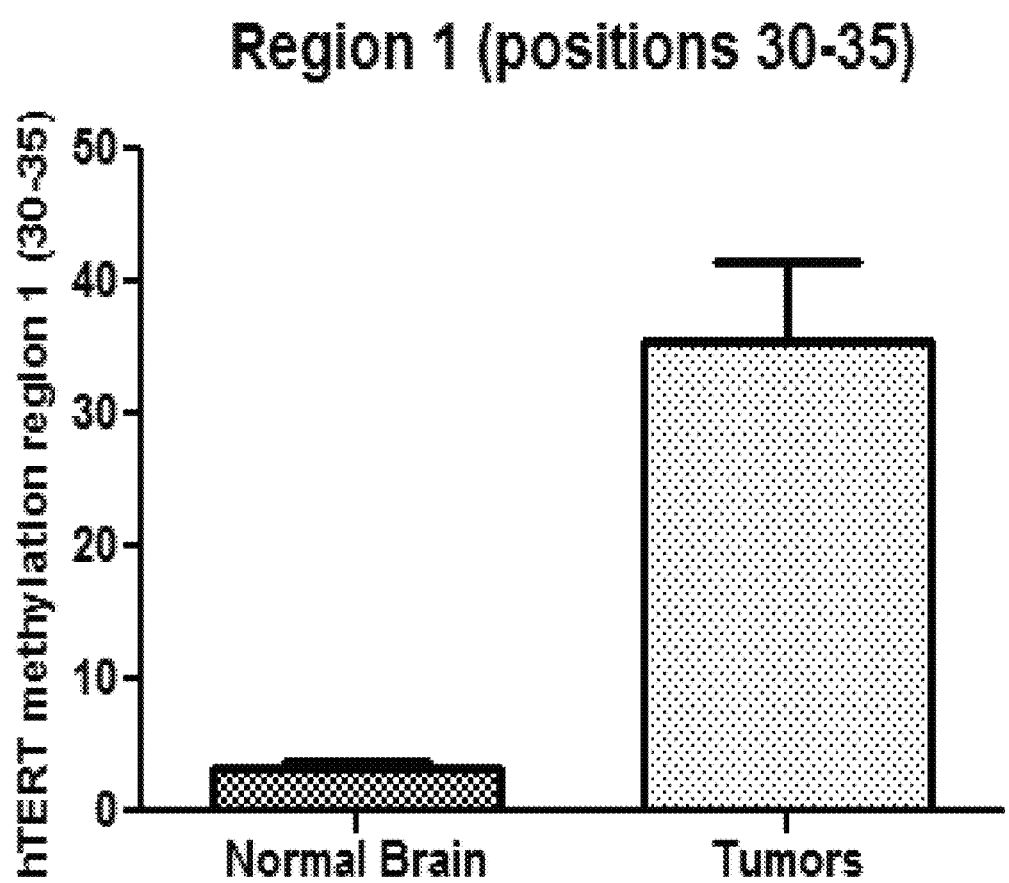
Figure 3D:
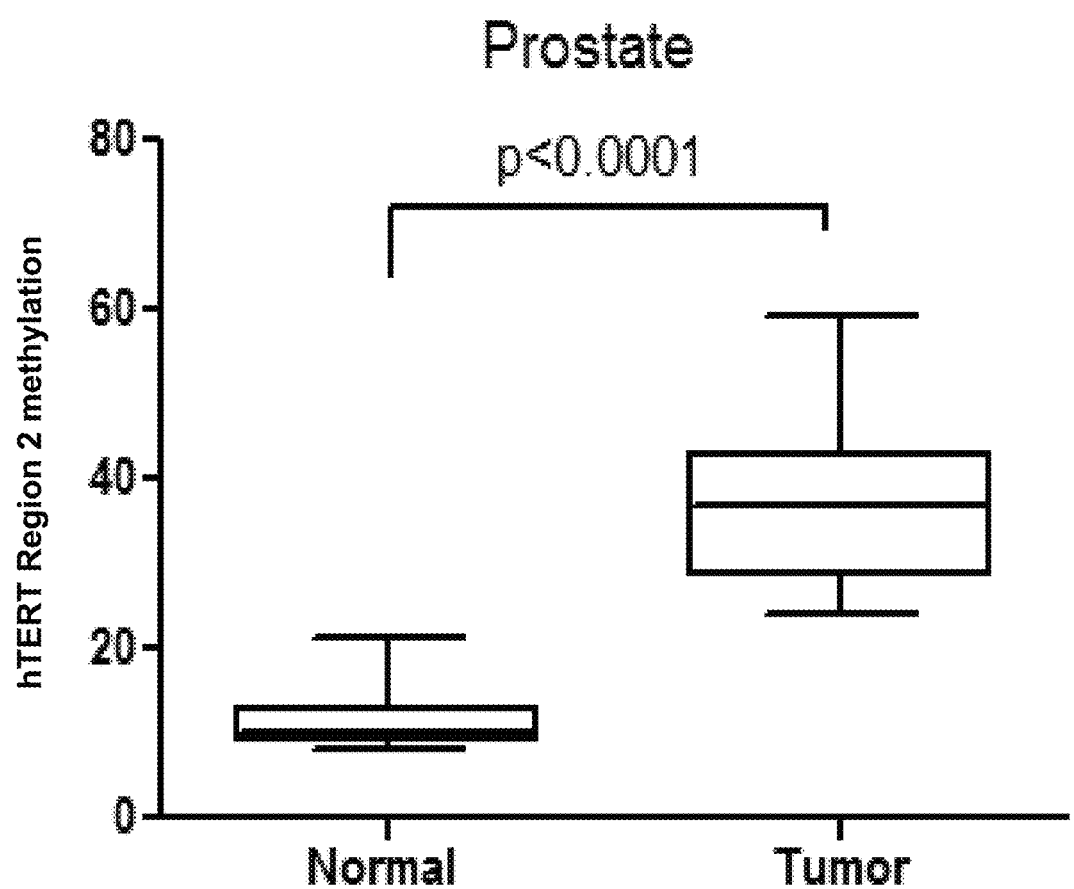

Pyrosequencing of additional regions 1A/B and 3 as identified above and shown in FIG. 1B also indicated lack of methylation in normal tissue versus significant methylation (hypermethylation) in tumour and cancerous samples across each of regions 1, 2 and 3 (see FIG. 3B). Thus, the target region within the hTERT promoter for use to distinguish between normal and cancerous samples is within about nucleotides at positions −157 to −580 of hTERT. Significant hypermethylation of the region 1 was observed in patient-derived tumour samples (high grade gliomas, leukemias and colon cancer) (P<0.0001) and cancer cell lines (cancer and tumour initiating cell lines) (P<0.0001) when compared to normal tissue samples as determined using pyrosequencing (FIG. 3C). A significant difference in methylation between normal prostate (n=50) and prostate cancer samples (n=50) was also found within region 2 of the hTERT promoter using pyrosequencing analysis (FIG. 3D).

Figure 4A:
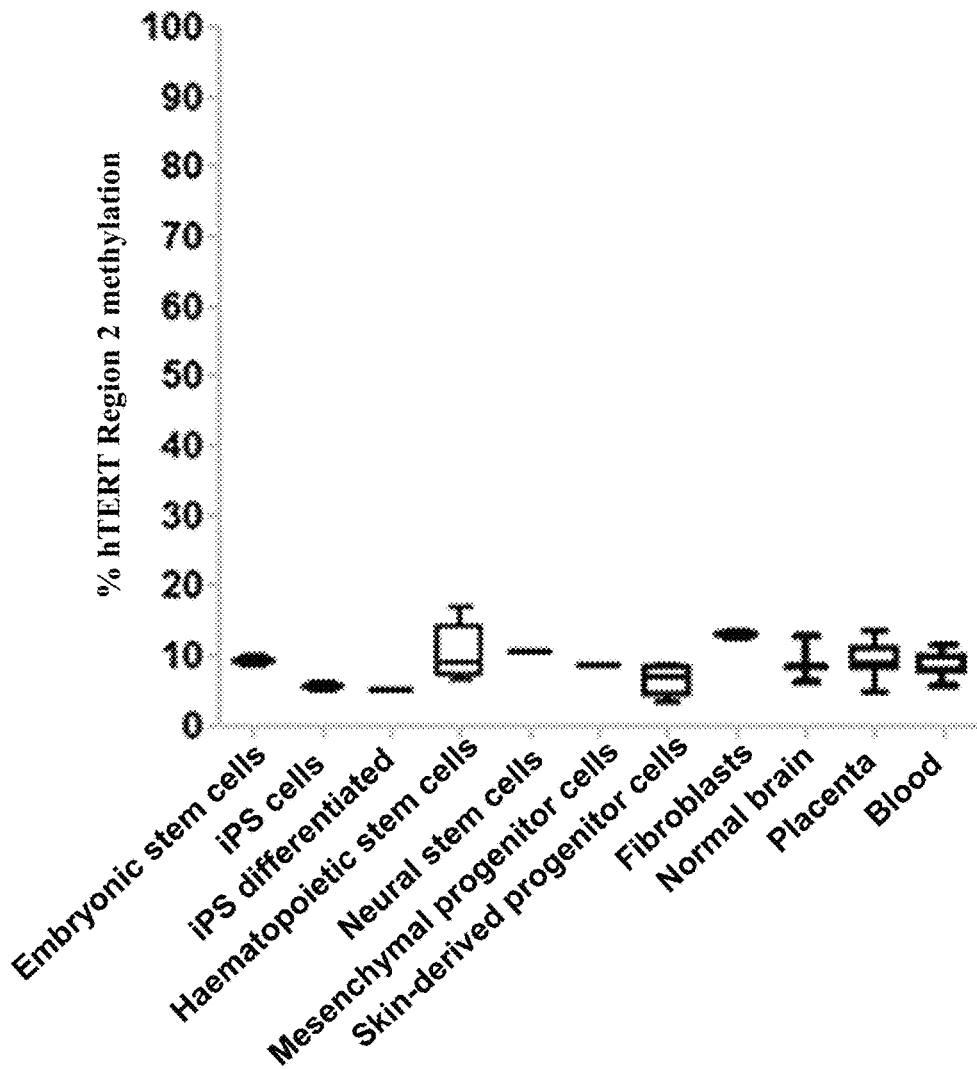
FIG. 4 graphically illustrates the methylation in region 2 of hTERT (A) and hTERT expression (B) in normal tissue and cultured cells, and the methylation at region 2 of hTERT (C) and hTERT expression (D) in tumour tissues and cancer cell lines.
Figure 4B:
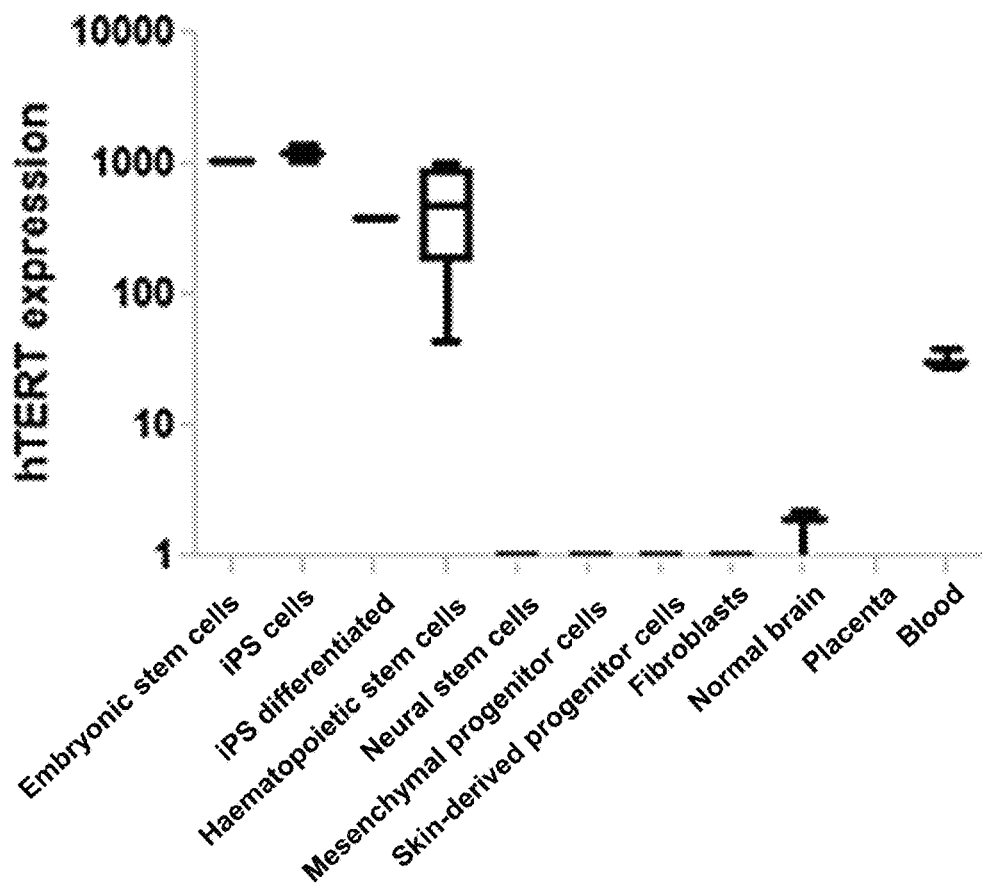
Figure 4C:
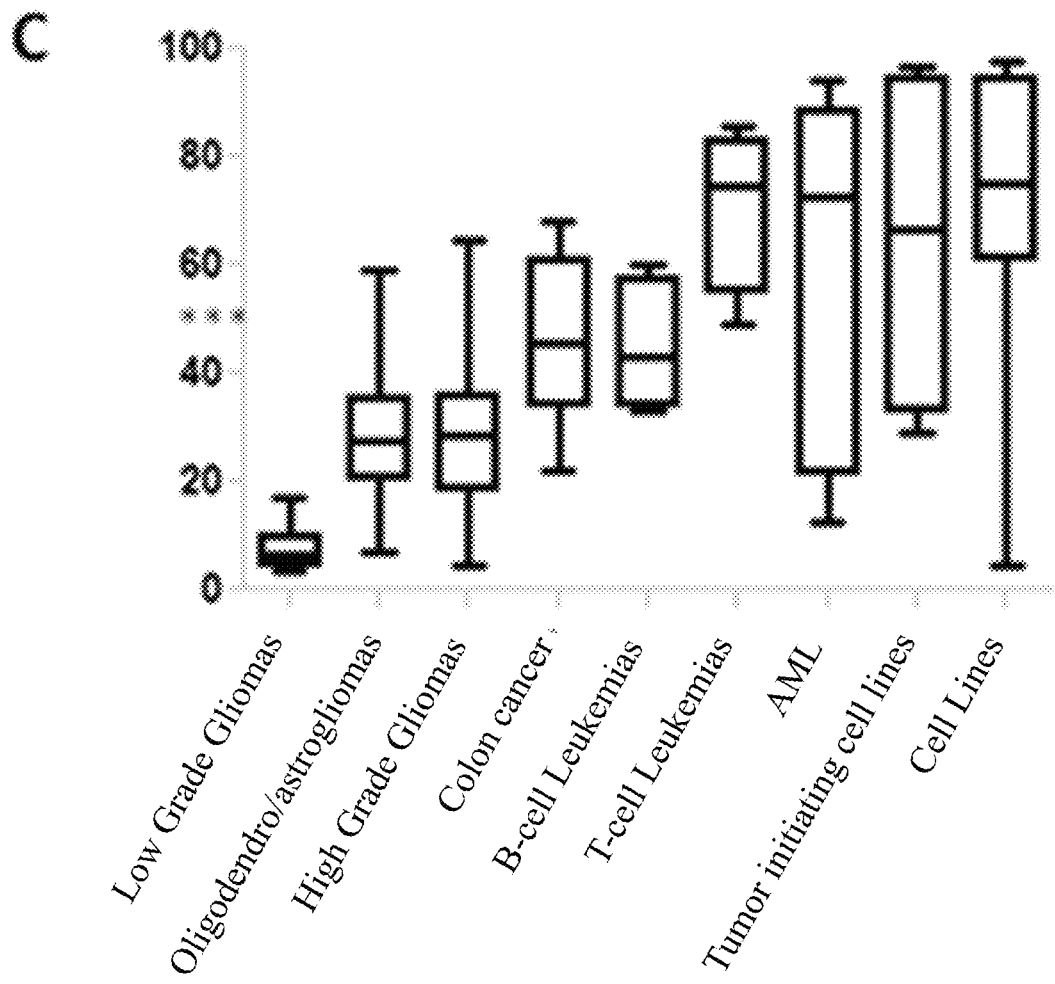
Figure 4D:
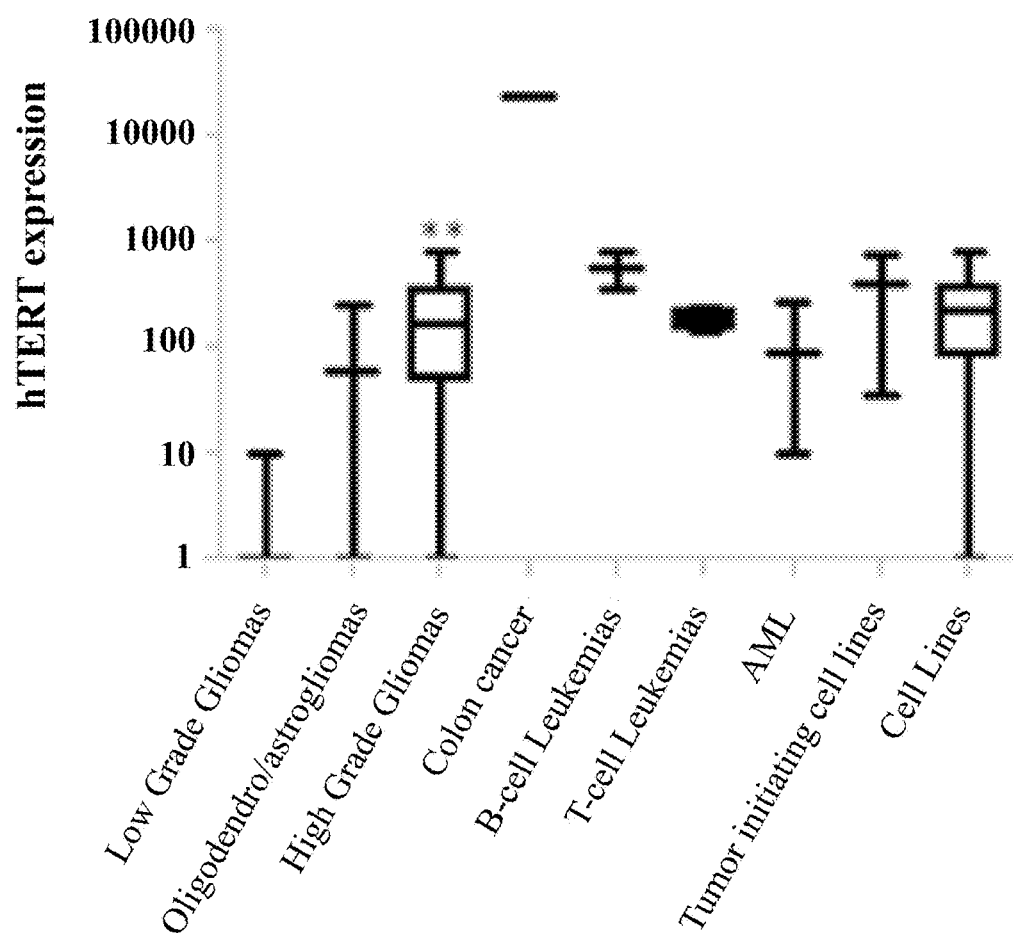

Methylation of Region 2 of hTERT Correlates with High hTERT Expression in Cancer Since not all cancers exhibit hTERT expression, the correlation between methylation within region 2 of hTERT and hTERT expression was analyzed in multiple normal tissues and tumours. As expected, several normal tissues—including embryonic stem cells, hematopoietic progenitors and blood lymphocytes—possessed variable levels of hTERT expression. However, these tissues did not display methylation within region 2 of hTERT (FIG. 4A, 4B). When a similar analysis was performed for malignant tissues—including pediatric and adult high grade gliomas, leukemias, colon cancer and multiple cancer cell lines—there was a strong correlation between methylation in region 2 of hTERT and high hTERT expression. Conversely, low grade pediatric tumours and low grade adult gliomas, which lack hTERT expression, showed no methylation in this region (FIG. 4C, 4D). The sensitivity and specificity of this assay to detect cancer tissues were 93% and 100%, respectively. Furthermore, the sensitivity increased to 96% when only hTERT-expressing cancers were considered. This resulted in positive predictive value of 1.0 and negative predictive value of 0.93 for methylation in region 2 of the hTERT promoter to detect malignancy in the cohort. Together these observations indicate that in cancer, there is a direct correlation between hTERT expression and hypermethylation in the TERT promoter.

Methylation in Region 2 of hTERT Increases with Tumour Progression

Figure 5A:
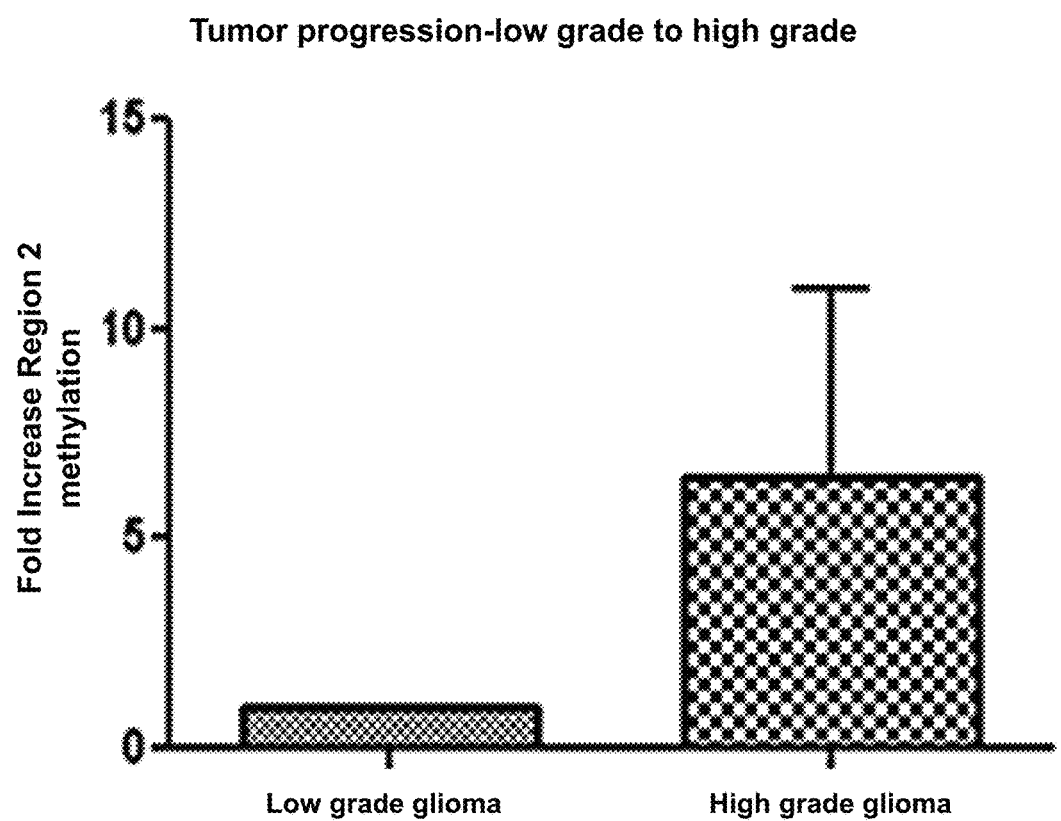
FIG. 5 graphically illustrates the effect on hTERT methylation in region 2 of hTERT in a low grade glioma compared to methylation in a glioma from the same patient that progressed to high grade (A) and the corresponding effect on hTERT expression (B), as well as the effect on hTERT methylation in region 2 of hTERT in adrenocortical carcinoma at primary and metastatic sites (C)
Figure 5B:
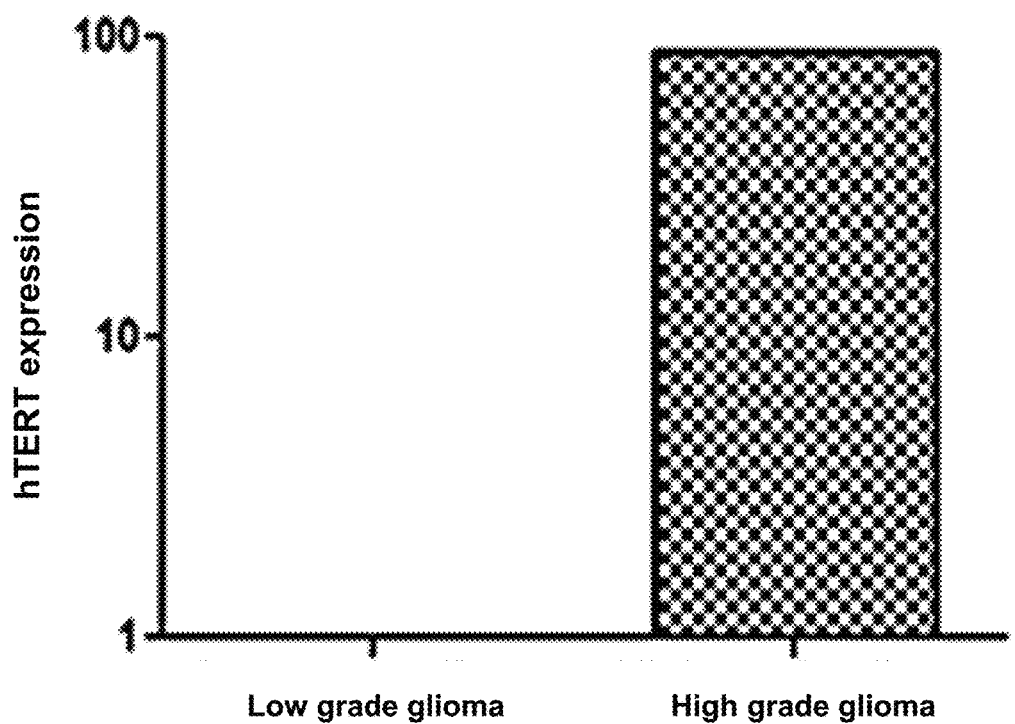
Figure 5C:
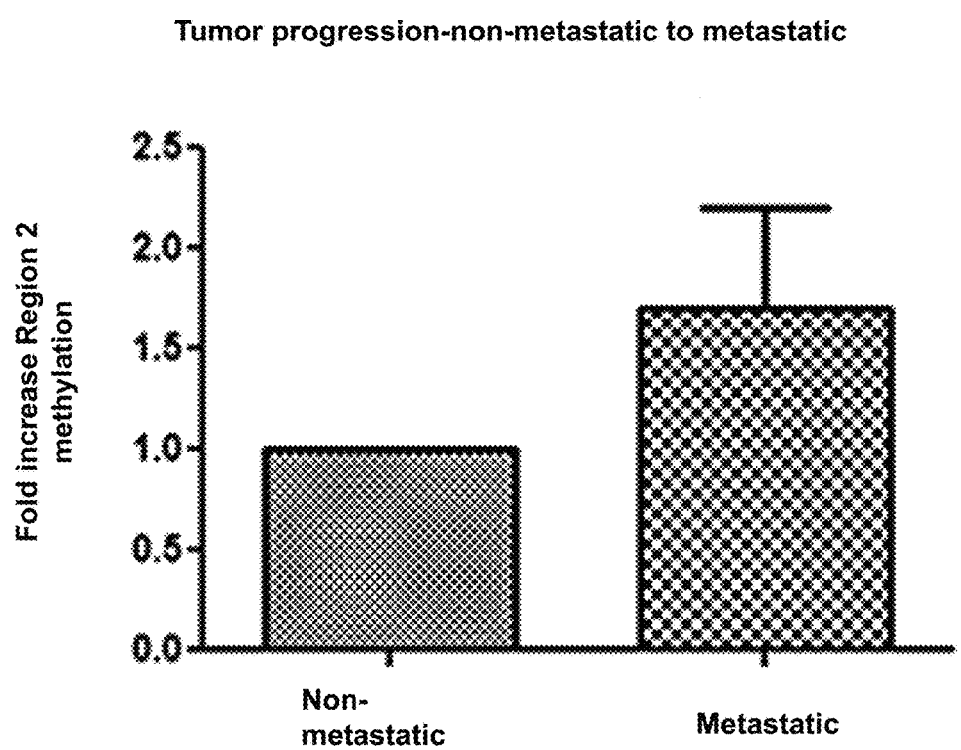

The lack of methylation within region 2 of hTERT in low-grade tumour cells was investigated to determine if methylation status changes during tumourigenesis. Samples from glioma patients whose disease had evolved from low to high grade were first analyzed. In all patients, low grade tumours exhibited low levels of hTERT methylation in region 2, while the corresponding transformed high grade cancers had higher methylation status in this region (FIG. 5A). Moreover, this increase in methylation was accompanied by an increase in hTERT expression (FIG. 5B). Samples from adrenocortical cancer patients whose tumours had progressed from localized to metastatic disease were then analyzed. Although both localized and metastatic tumour samples showed higher levels of hTERT methylation in region 2 than their corresponding normal tissues, the paired samples from the same patient revealed an increase in hTERT methylation in region 2 with progression to metastatic disease (FIG. 5C).

Figure 6A:
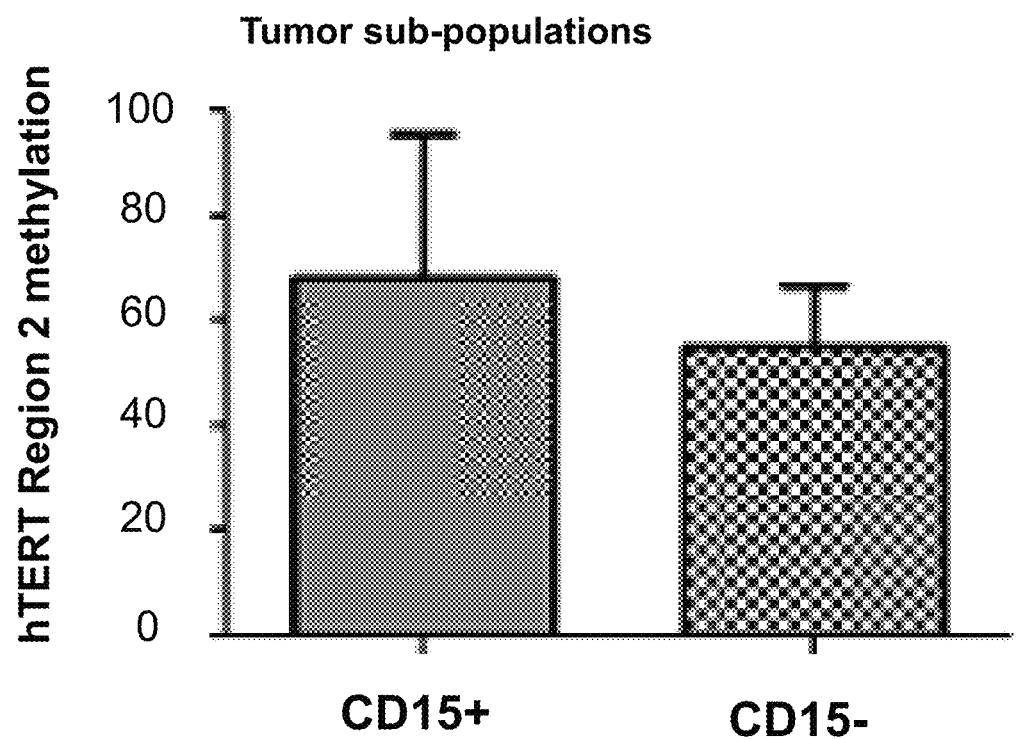
FIG. 6 graphically illustrates methylation analysis of cells from freshly resected high-grade gliomas (G404 and TB1) after FACS cell sorting based on CD15/SSEA1 expression (A); correlation between an increase in differential allelic expression (DAE) and methylation (B); decreased methylation (less than 30%) in tumour samples correlates with reduced hTERT monoallelic expression when compared to samples with 30-70% methylation (C); and increased region 2 methylation correlates with an increase in hTERT expression (D)
Figure 6B:
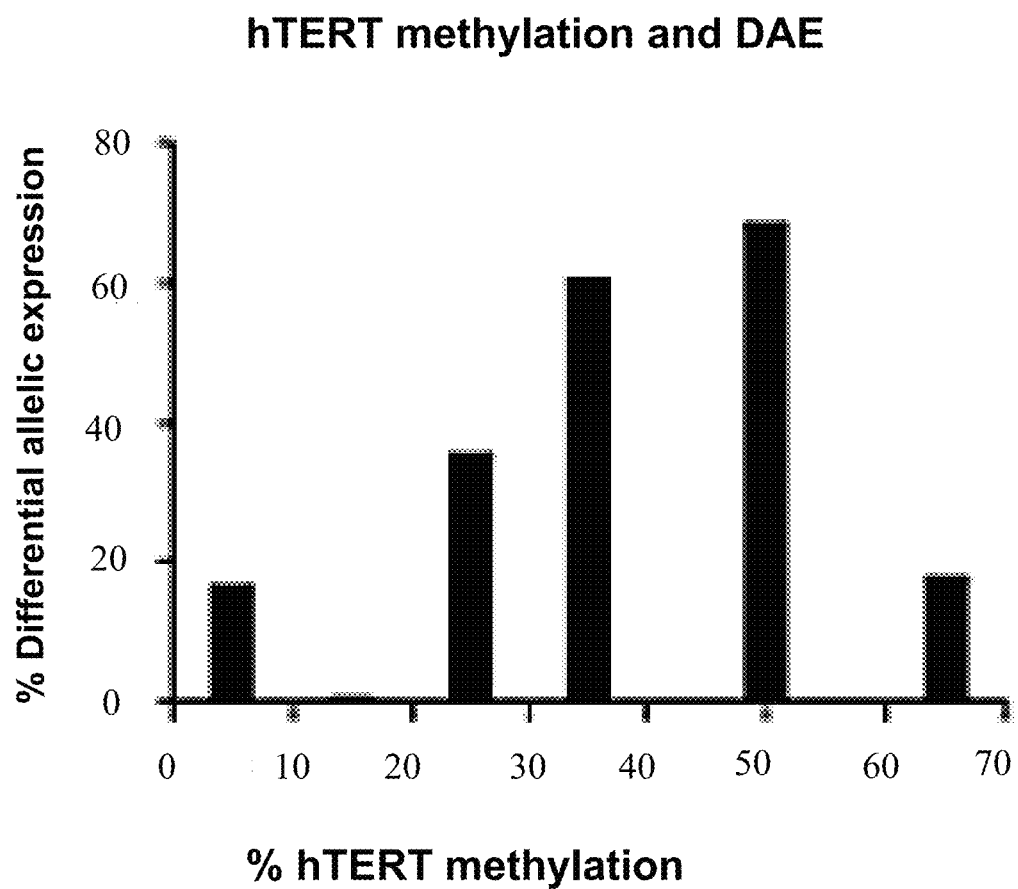
Figure 6C:
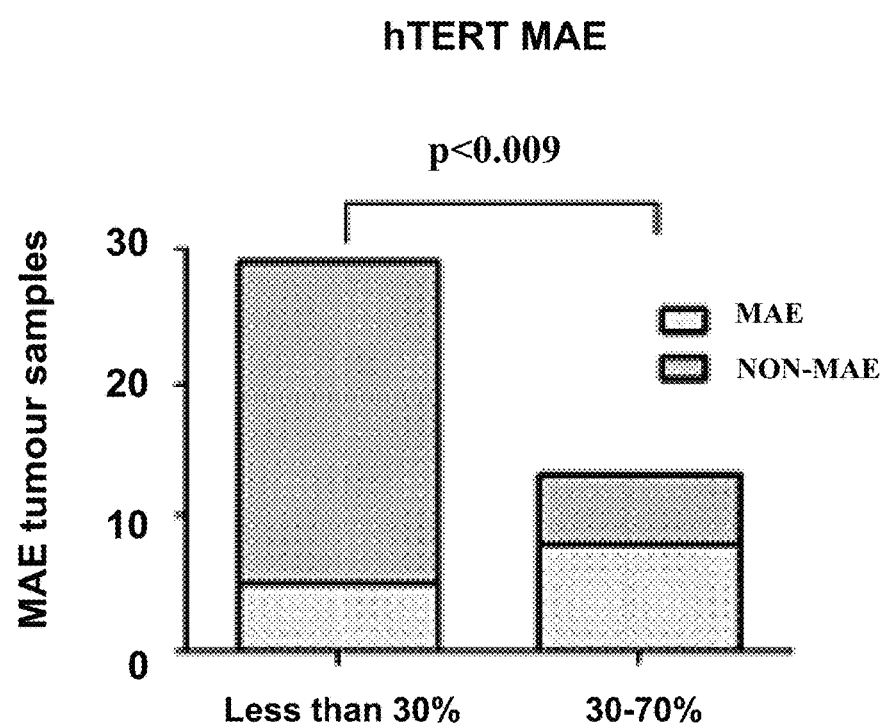
Figure 6D:
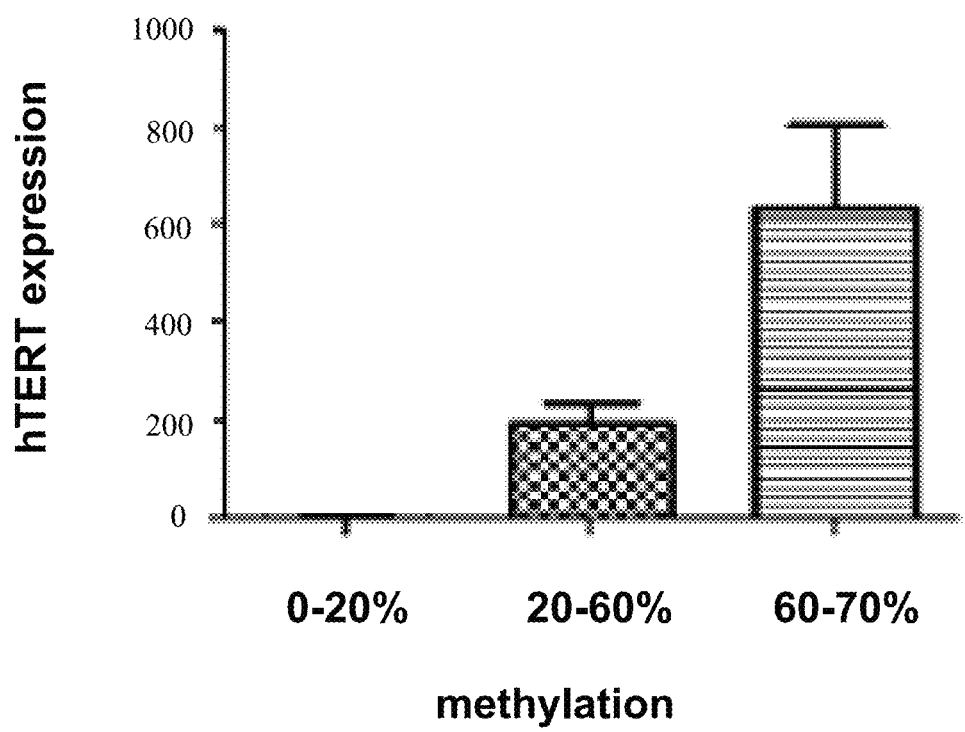

The transition from low to high methylation status in region 2 of hTERT could occur either as a dynamic process in all cancer cells or as a result of clonal evolution. To determine which of these two possibilities was the case, freshly resected gliomas were separated into tumor subpopulations using CD15/SSEA1 as a marker to identify an enriched population of tumor initiating cells (TICs) from the bulk of tumor cells. The CD15-positive TIC subpopulation was previously demonstrated to possess higher hTERT expression than the bulk of tumor cells. Both sub-populations of tumor cells showed similar levels of hTERT methylation in this region (FIG. 6A) indicating that increased methylation over time is not due to a highly methylated clone which is enriched as tumor progression occurs. Sequenom® technology was then used to determine whether the extent of hTERT methylation could result in differential hTERT allelic expression. Differential allelic expression of hTERT was found to be common in gliomas. Interestingly, as methylation increased from 0 to 50% in region 2, the difference in allelic expression also increased to a maximum at 50% methylation (FIG. 6B). This was followed by a decrease in differential allelic expression when methylation in region 2 exceeded 50%. These findings suggest that hTERT methylation is initially restricted to one allele resulting in monoallelic expression of this allele, and then, as the tumor progresses, the other allele is hypermethylated resulting in loss of monoallelic expression (FIG. 6B). Monoallelic expression of hTERT was significantly less common in tumors with less than 30% methylation in region 2 than those with higher methylation in this region (P<0.009) (FIG. 6C). Finally, levels of methylation in region 2 strongly correlated with levels of hTERT expression (FIG. 6D) even when differential expression decreased suggesting that methylation of the second allele results in even higher hTERT expression. These results indicate that hypermethylation within the hTERT promoter is a dynamic process occurring in the majority of cancer cells to allow for higher hTERT expression during tumor progression.

Treatment with Demethylating Agents Decreases hTERT Expression

Figure 7A:
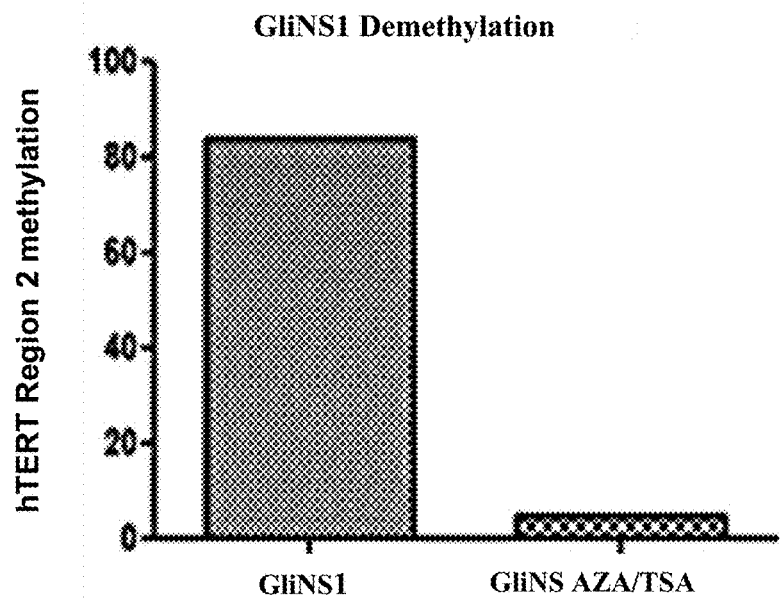
FIG. 7 graphically illustrates the effect of demethylation therapy in region 2 of the hTERT promoter in GLiNS1 glioma tumour-initiating cells (A) and UW228 medulloblastoma cells (C) and on hTERT expression in each case (respectively B, D) in comparison to the effect of demethylation (E) on hTERT expression (F) in embryonic stem cell controls.
Figure 7B:
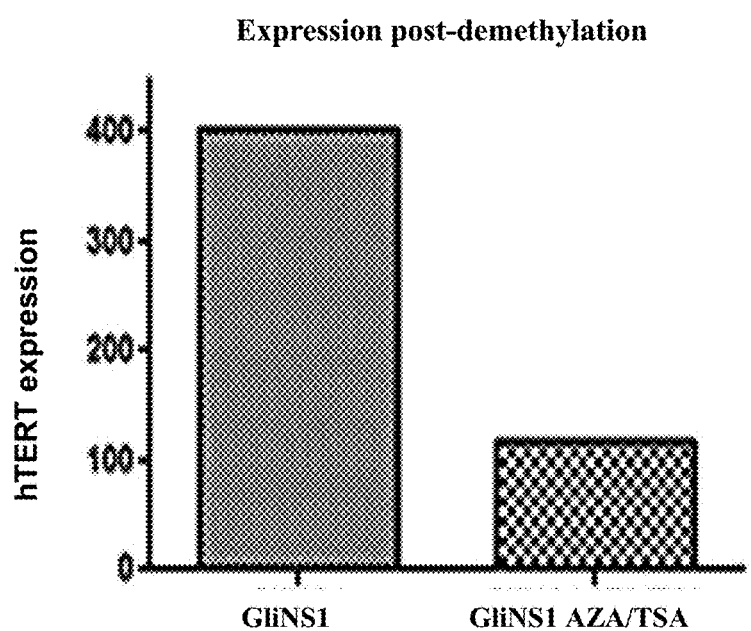
Figure 7C:
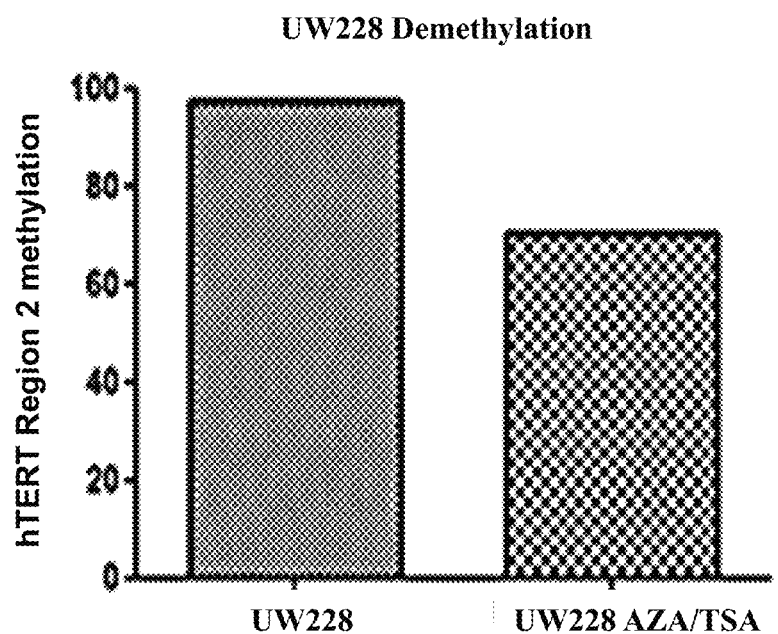
Figure 7D:
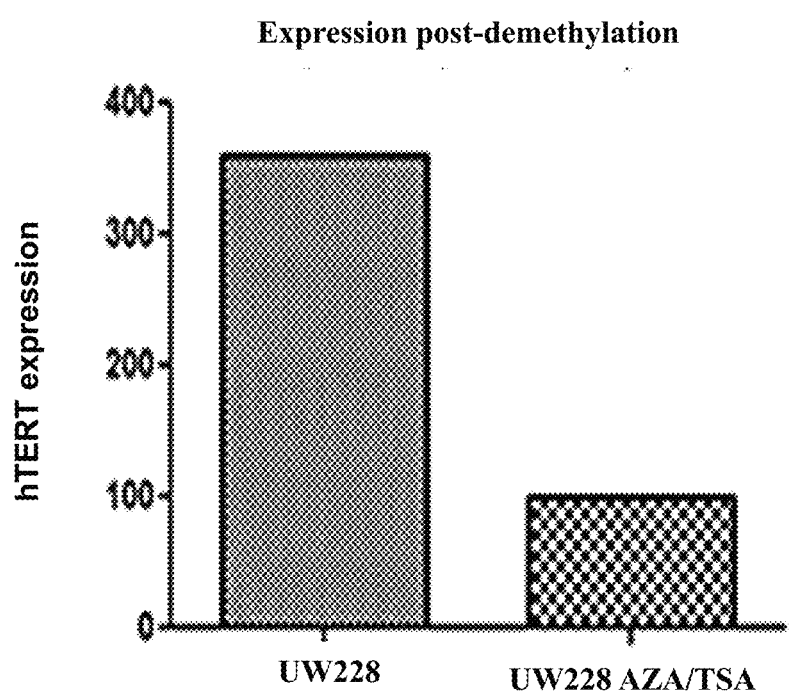
Figure 7E:
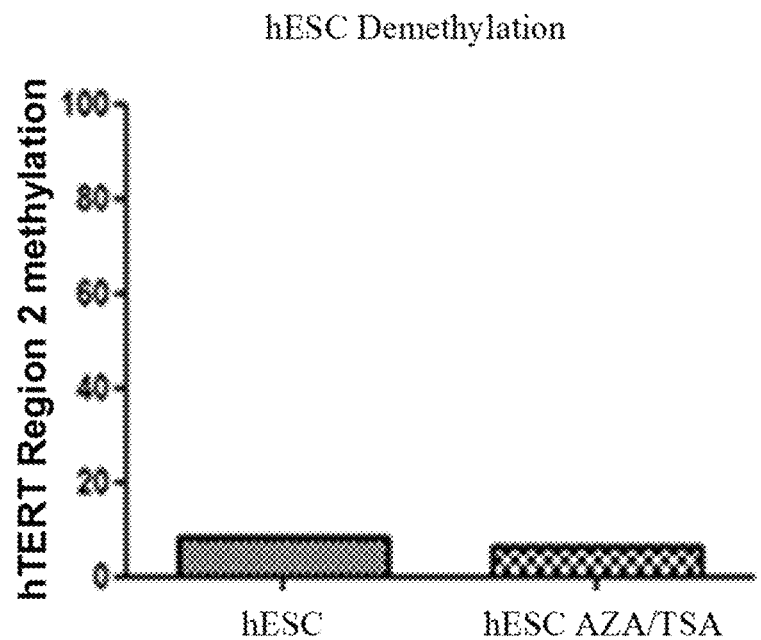
Figure 7F:
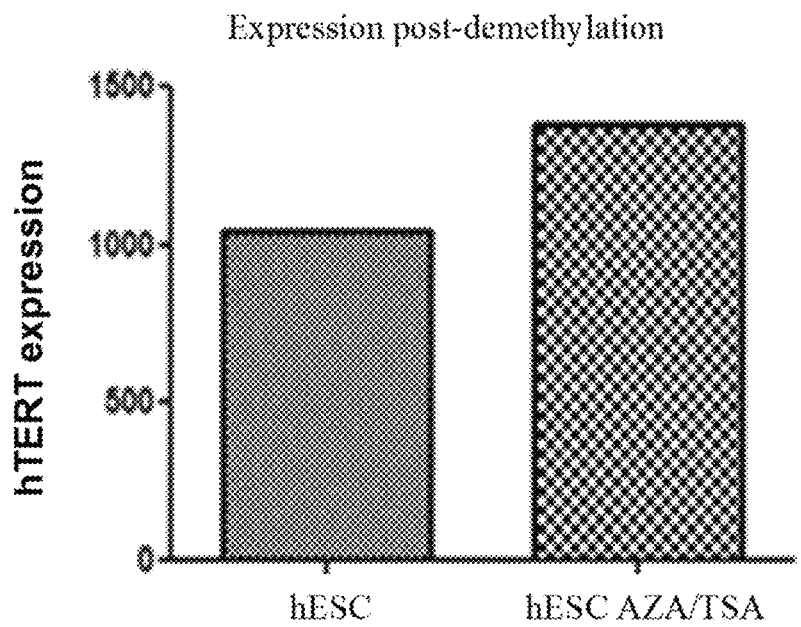

Since methylation was found to correlate with higher hTERT expression in cancer cells, it was determined whether or not treatment of tumor cells with demethylating agents might decrease hTERT expression. Glioma (GLINS1) and medulloblastoma (UW228) cell lines were treated with 5-azacytidine (5AZA) in combination with Trichostatin A (TSA). A decrease in hTERT methylation in region 2 of hTERT was observed in both cell lines (FIG. 7A, 7B) and this correlated with a decrease in hTERT expression (FIG. 7C, 7D). When the same treatment was applied to embryonic stem cells no significant changes in hTERT expression were observed (7E, 7F), indicating that hTERT expression is regulated by an alternative mechanism in normal stem cells. This finding also indicates that demethylating agents are useful for the treatment of hTERT-expressing tumors without negatively affecting normal stem cells.

Methylation Status Predicts Tumour Sub-Type

Methylation in hTERT was found to differ across tumour sub-types. Choroid plexus papillomas showed low methylation within region 2 of hTERT whereas carcinomas showed higher methylation. Atypical papillomas where divided into two subgroups: those with low promoter methylation that behaved like papillomas and those with high promoter methylation that progressed into carcinomas. It is noted that in the atypical papilloma group, the 2 patients that exhibited high promoter methylation with a progression of the papilloma to carcinoma both died.

Methylation Status Predictive of Patient Survival

Methylation in hTERT was also found to be predictive of patient survival. Using Sequenom® analysis, five year over all survival in ependymoma patients was 86+/−9% and 30+/−10% for patients having tumours which exhibited hypomethylation (n=20) and hypermethylation (n=25), respectively, within region 2 of hTERT (FIG. 8A). Five year progression-free survival was 95+/−5% and 51+/−10% for patients having tumours which exhibited hypomethylation (n=20) and hypermethylation (n=25), respectively (FIG. 8B).

Methylation Status Predictive of Treatment

Figure 9A:
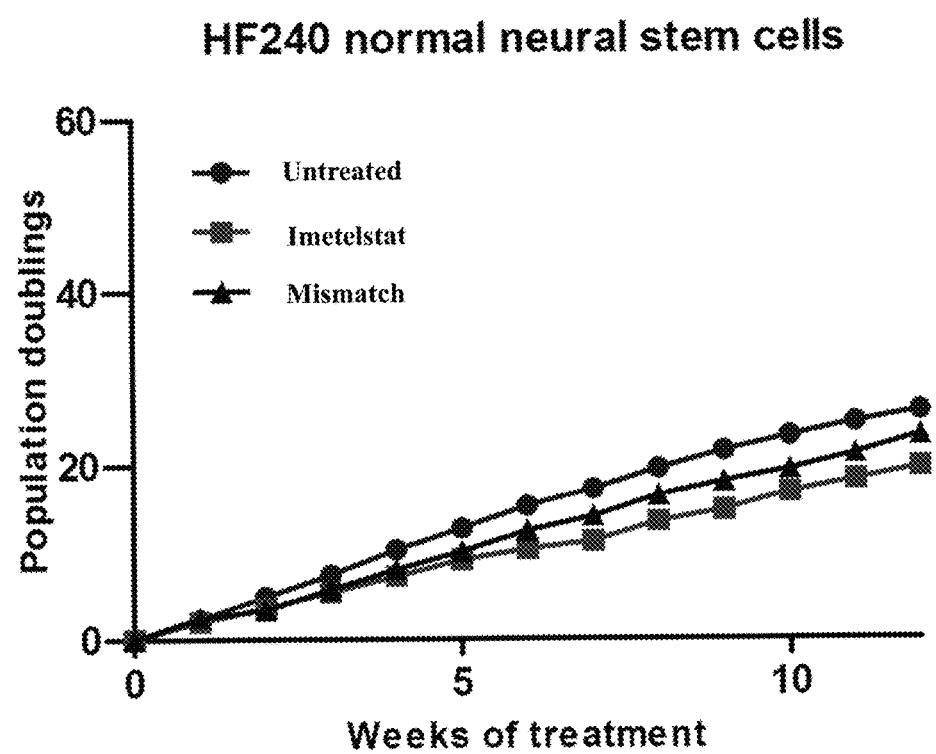
FIG. 9 graphically illustrates the effect of a telomerase inhibitor on normal neural stem cells (A) and glioma G179 tumour-initiating cells (B)
Figure 9B:
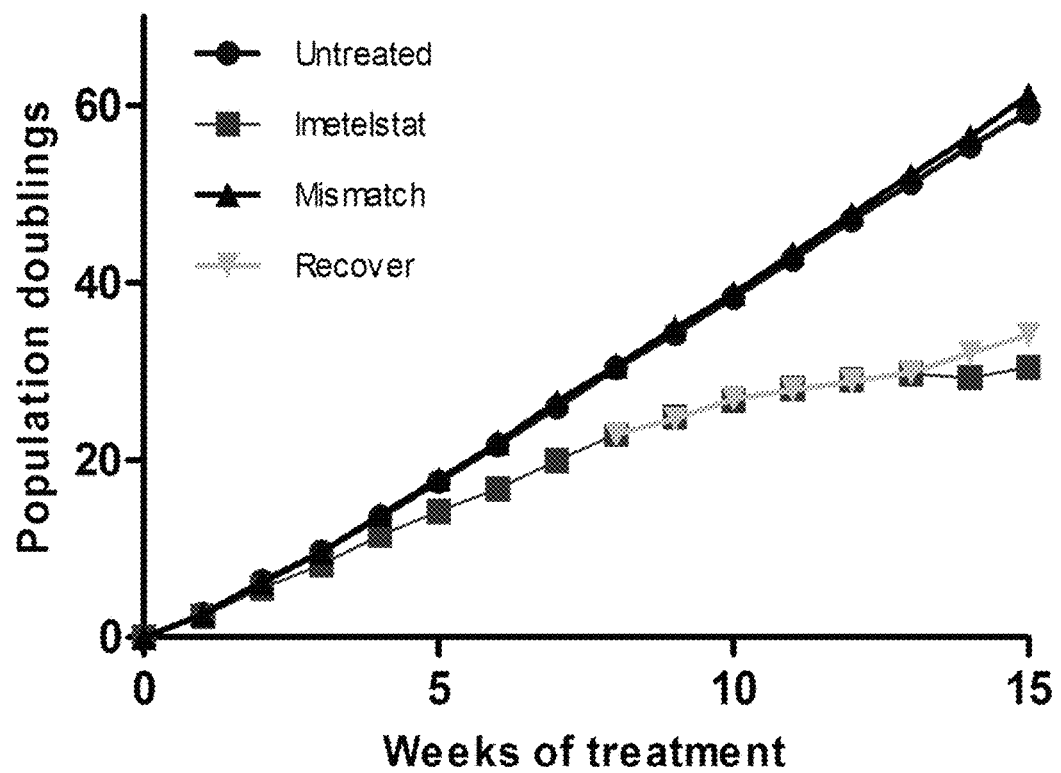

Methylation status within the target TERT promoter region is also predictive of suitable cancer treatment protocol. Administration of telomerase inhibitor, Imetelstat (5 μM), was found to inhibit growth of glioma tumour-initiating cells (TIC) but not normal neural stem cells as shown in FIG. 9. Only TICs show loss of replicative potential after telomerase inhibition. Data points represent the mean of triplicate cell counts+/−standard deviation.

Figure 10:
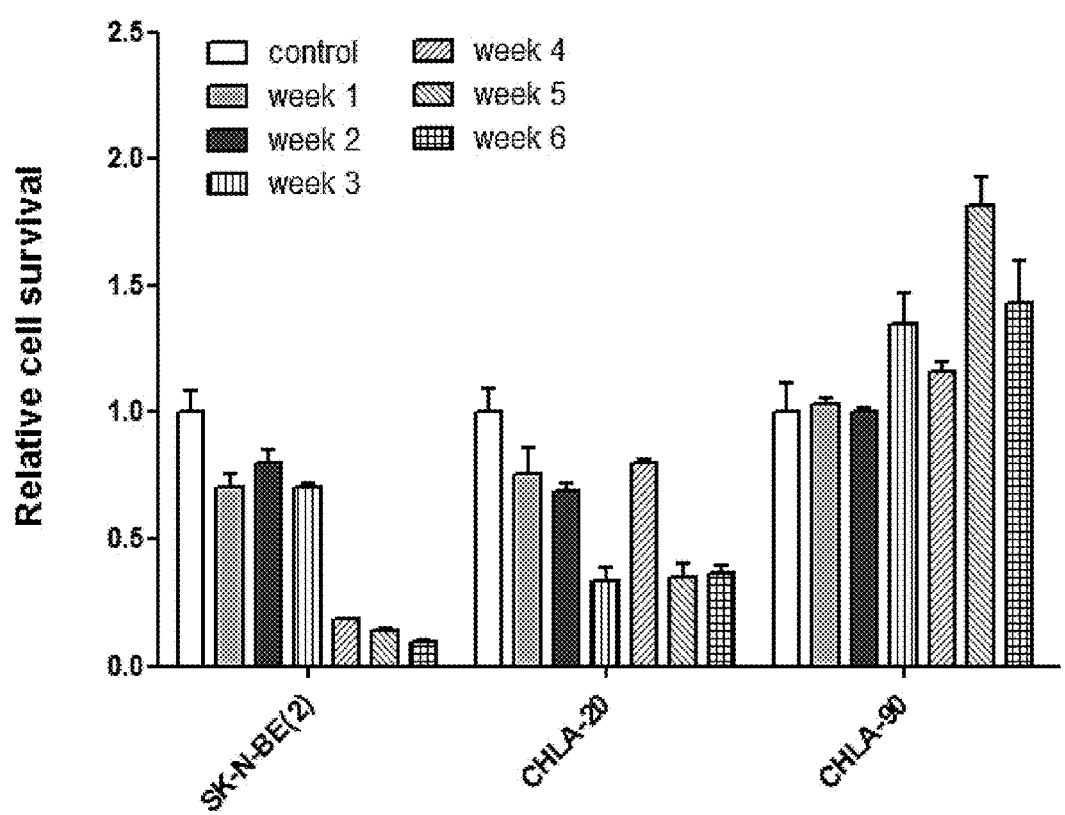
FIG. 10 graphically illustrates that treatment of hypermethylated neuroblastoma cells with imetelstat has an inhibitory effect on growth and viability, while treatment of unmethylated neuroblastoma cells did not.

A neuroblastoma cell line (CHLA90) that was found to be unmethylated within region 2 of the TERT promoter was treated, as well as two additional cell lines which demonstrated hypermethylation in this region, with Imetelstat (5 μM), for 5 weeks. Both hypermethylated cell lines responded to Imetelstat while the nonmethylated line did not (FIG. 10). This latter cell line also exhibited evidence of ALT. This indicates that hypermethylation within the TERT promoter can be used to determine which tumors do not require telomerase activity for telomere maintenance and therefore will not respond to telomerase inhibition.

Unmethylated Malignant Tumours Display an Alternative Lengthening of Telomeres (ALT) Phenotype Although most malignant tumours were extensively methylated in region 2 of the hTERT promoter, about ~10% of malignant gliomas were not, and these tumours did not express hTERT. It was therefore determined whether or not these tumours were maintaining their telomeres independent of telomerase activation and found that these tumours displayed aberrantly long telomeres consistent with an ALT phenotype. Gliomas demonstrating ALT had significantly lower methylation in the tested regions than those expressing telomerase (P<0.001). Tumours with the ALT phenotype and low levels of methylation in region 2 of the hTERT promoter were also observed amongst leukemias and in cancer cell lines and accounted for the majority of malignant cancers with low region 2 methylation. In contrast, all hTERT-expressing cancers (n=91) exhibited region 2 hypermethylation. These observations indicate that in malignant neoplasms, lack of methylation in region 2 of the hTERT promoter could be used as a screening tool to detect ALT.

What is claimed is:

1. A method of predicting tumour progression from benign to malignant, or the grade of a tumour, in a human and treating the human, comprising the steps of determining in a tumour sample from the human the degree of DNA methylation of CG sites within the TERT promoter to yield a sample methylation signature; determining the baseline degree of DNA methylation of the TERT promoter in a control sample to yield a control methylation signature; comparing the sample methylation signature to the control methylation signature and identifying a tumour to be a malignant tumour when there is at least 1.5 times more methylation in the sample methylation signature in a region of the hTERT promoter consisting of from the nucleotide at about position −157 to the nucleotide at about position −580 as compared to the control methylation signature; and treating the human with one of a telomerase-targeted therapy or a demethylation therapy.

2. The method of claim 1, wherein there is at least 2 times more methylation in the sample methylation signature as compared to the control methylation signature.

3. The method of claim 1, wherein there is at least 3 times more methylation in the sample methylation signature as compared to the control methylation signature.

4. The method of claim 1, wherein the methylated CG sites are contiguous.

5. The method of claim 1, wherein the telomerase-targeted therapy is selected from Imetelstat and telomestatin.

6. The method of claim 1, wherein the demethylation therapy is selected from the group consisting of 5-azacytidine and derivatives thereof.

7. A method of predicting tumour progression from benign to malignant, or the grade of a tumour, in a human comprising the steps of:
   determining in a tumour sample from the human the degree of DNA methylation of CG sites within the TERT promoter to yield a sample methylation signature and determining the baseline degree of DNA methylation of the TERT promoter in a control sample to yield a control methylation signature, wherein the degree of methylation is determined using one or more of the primers selected from the group consisting of PCR primers, aggaagagagGGGAAGTGTTGTAGGGAGG-TATTT (SEQ ID NO: 4), cagtaatacgactcactataggga-gaaggctAAAACCATAATATAAAAACCC-TAAA (SEQ ID NO: 5), TTGGAAGGTGAAGGGGTAG (SEQ ID NO: 9); PCR primers, TATGATGTGGAG-GTTTTGGG (SEQ ID NO: 10), and GGTGAAGGGG-TAGGA (SEQ ID NO: 11), and pyrosequencing primer, GGATTAGGGGGTTTG (SEQ ID NO: 12); PCR primers, ATGATGTGGAGGTTTTGGGAATAG (SEQ ID NO: 14), and CCCAACCTAAAAACAACCCTAAAT (SEQ ID NO: 15), and pyrosequencing primer, GGAG-GTTTTGGGAATAG (SEQ ID NO: 16); and PCR primers, GGTTTGATTYGGAGATTTAGGGTTGTTT (SEQ ID NO: 18), AGAAAGGGTGGGAAATGGA (SEQ ID NO: 19) and pyrosequencing primer, GAG-GAAGTATTGTTT (SEQ ID NO: 20); comparing the sample methylation signature to the control methylation signature, and identifying a tumour to be a malignant tumour when there is at least 1.5 times more methylation in the sample methylation signature in a region of the hTERT promoter from the nucleotide at about position −157 to the nucleotide at about position −580.

8. The method of claim 7, wherein there is at least 2 times more methylation in the sample methylation signature as compared to the control methylation signature.

9. The method of claim 7, wherein there is at least 3 times more methylation in the sample methylation signature as compared to the control methylation signature.

10. The method of claim 7, wherein the methylated CG sites are contiguous.

* * * * *

SEQUENCE LISTING

```
<160> NUMBER OF SEQ ID NOS: 20

<210> SEQ ID NO 1
<211> LENGTH: 1000
<212> TYPE: DNA
<213> ORGANISM: Homo sapiens

<400> SEQUENCE: 1
gctgcgcagc agggagcgca cggctcggca gcggggagcg cgcggcatcg cggggggtggc      60 cggggccagg gcttcccacg tgcgcagcag gacgcagcgc tgcctgaaac tcgcgccgcg     120
aggagagggc ggggccgcgg aaaggaaggg gaggggctgg gagggcccgg aggggggctgg     180 gccgggggacc cgggagggggt cgggacgggg cgggtccgc gcggaggagg cggagctgga     240
aggtgaaggg gcaggacggg tgcccgggtc cccagtccct ccgccacgtg ggaagcgcgg     300
tcctgggcgt ctgtgcccgc gaatccactg ggagcccggc ctggccccga cagcgcagct     360
gctccgggcg gacccggggg tctgggccgc gcttcccgc ccgcgcgccg ctcgcgctcc     420
cagggtgcag ggacgccagc gagggcccca gcggagagag gtcgaatcgg cctaggctgt     480
ggggtaaccc gagggagggg ccatgatgtg gaggccctgg gaacaggtgc gtgcggcgac     540
cctttggccg ctggcctgat ccggagaccc agggctgcct ccaggtccgg acgcggggcg     600
tcgggctccg ggcaccacga atgccggacg tgaagggag gacggaggcg cgtagacgcg     660
gctggggacg aacccgagga cgcattgctc cctggacggg cacgcgggac ctcccggagt     720
gcctccctgc aacacttccc cgcgacttgg gctccttgac acaggcccgt catttctctt     780
tgcaggttct caggcggcga ggggtcccca ccatgagcaa accacccaa atctgttaat     840 cacccaccgg ggcggtcccg tcgagaaagg gtgggaaatg gagccaggcg ctcctgctgg     900
ccgcgcaccg ggcgcctcac accagccaca acggccttga ccctgggccc cggcactctg     960
tctggcagat gaggccaaca tctggtcaca tcccgcccgc                          1000
```

```
<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgacacctca cctcacccac                                              20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cactgtcttc cgcaagttca c                                            21

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
aggaagagag gggaagtgtt gtagggaggt attt                              34

<210> SEQ ID NO 5
<211> LENGTH: 56
<212> TYPE: DNA
<213> ORGANISM: Artificial Sequence
<220> FEATURE:
<223> OTHER INFORMATION: primer

<400> SEQUENCE: 5
cagtaatacg actcactata gggagaaggc taaaaccata atataaaaac cctaaa      56

<210> SEQ ID NO 6
<211> LENGTH: 216
<212> TYPE: DNA
<213> ORGANISM: Homo sapiens

<400> SEQUENCE: 6
ccatgatgtg gaggccctgg aacaggtgc gtgcggcgac cctttggccg ctggcctgat    60
ccggagaccc agggctgcct ccaggtccgg acgcggggcg tcgggctccg ggcaccacga  120
atgccggacg tgaaggggag gacggaggcg cgtagacgcg gctggggacg aacccgagga  180
cgcattgctc cctggacggg cacgcgggac ctcccg                            216

<210> SEQ ID NO 7
<211> LENGTH: 109
<212> TYPE: DNA
<213> ORGANISM: Homo sapiens

<400> SEQUENCE: 7
cgggtgcccg ggtccccagt ccctccgcca cgtgggaagc gcggtcctgg gcgtctgtgc    60
ccgcgaatcc actgggagcc cggcctggcc ccgacagcgc agctgctcc               109

<210> SEQ ID NO 8
<211> LENGTH: 90
<212> TYPE: DNA
```

<213> ORGANISM: Homo sapiens

<400> SEQUENCE: 8
ggccgcgctt ccccgcccgc gcgccgctcg cgctcccagg gtgcagggac gccagcgagg    60
gccccagcgg agagaggtcg aatcggccta    90

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
ttggaaggtg aagggggtag    19

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tatgatgtgg aggttttggg    20

<210> SEQ ID NO 11
<211> LENGTH: 15
<212> TYPE: DNA
<213> ORGANISM: Artificial Sequence
<220> FEATURE:
<223> OTHER INFORMATION: primer

<400> SEQUENCE: 11
ggtgaagggg tagga    15

<210> SEQ ID NO 12
<211> LENGTH: 15
<212> TYPE: DNA
<213> ORGANISM: Artificial Sequence
<220> FEATURE:
<223> OTHER INFORMATION: primer

<400> SEQUENCE: 12
ggattagggg gtttg    15

<210> SEQ ID NO 13
<211> LENGTH: 42
<212> TYPE: DNA
<213> ORGANISM: Homo sapiens

<400> SEQUENCE: 13
gtgcgtgcgg cgacccttttg gccgctggcc tgatccggag ac    42

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
atgatgtgga ggttttggga atag    24

```
<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
cccaacctaa aaacaaccct aaat                                          24

<210> SEQ ID NO 16
<211> LENGTH: 17
<212> TYPE: DNA
<213> ORGANISM: Artificial Sequence
<220> FEATURE:
<223> OTHER INFORMATION: primer

<400> SEQUENCE: 16
ggaggttttg ggaatag                                                  17

<210> SEQ ID NO 17
<211> LENGTH: 114
<212> TYPE: DNA
<213> ORGANISM: Homo sapiens

<400> SEQUENCE: 17
cctggacggg cacgcgggac ctcccggagt gcctccctgc aacacttccc cgcgacttgg   60
gctccttgac acaggcccgt catttctctt tgcaggttct caggcggcga gggg        114

<210> SEQ ID NO 18
<211> LENGTH: 28
<212> TYPE: DNA
<213> ORGANISM: Artificial Sequence
<220> FEATURE:
<223> OTHER INFORMATION: primer

<400> SEQUENCE: 18
ggtttgatty ggagatttag ggttgttt                                      28

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
agaaagggtg ggaaatgga                                                19

<210> SEQ ID NO 20
<211> LENGTH: 15
<212> TYPE: DNA
<213> ORGANISM: Artificial Sequence
<220> FEATURE:
<223> OTHER INFORMATION: primer

<400> SEQUENCE: 20
gaggaagtat tgttt                                                    15
```